US009670271B2

(12) United States Patent
Lin et al.

(10) Patent No.: US 9,670,271 B2
(45) Date of Patent: *Jun. 6, 2017

(54) PRODUCTION OF RECOMBINANT PROTEINS WITH SIMPLE GLYCOFORMS

(71) Applicant: SIGMA-ALDRICH CO. LLC, St. Louis, MO (US)

(72) Inventors: Nan Lin, St. Louis, MO (US); Natalie Sealover, St. Louis, MO (US); Henry George, St. Louis, MO (US); Kevin Kayser, St. Louis, MO (US)

(73) Assignee: SIGMA-ALDRICH CO. LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/171,977

(22) Filed: Jun. 2, 2016

(65) Prior Publication Data
US 2016/0272696 A1 Sep. 22, 2016

Related U.S. Application Data

(63) Continuation of application No. 14/371,137, filed as application No. PCT/US2013/020947 on Jan. 10, 2013, now Pat. No. 9,376,484.

(60) Provisional application No. 61/585,508, filed on Jan. 11, 2012, provisional application No. 61/636,680, filed on Apr. 22, 2012, provisional application No. 61/720,268, filed on Oct. 30, 2012.

(51) Int. Cl.
C12P 21/02 (2006.01)
C07K 16/10 (2006.01)
C12P 21/00 (2006.01)
C12N 9/10 (2006.01)
C07K 16/00 (2006.01)
C12P 21/04 (2006.01)
C12N 15/63 (2006.01)
C12N 15/67 (2006.01)
C12N 15/85 (2006.01)

(52) U.S. Cl.
CPC ............ C07K 16/10 (2013.01); C07K 16/00 (2013.01); C12N 9/1051 (2013.01); C12P 21/005 (2013.01); C12P 21/02 (2013.01); C12Y 204/01101 (2013.01); C07K 2317/14 (2013.01); C07K 2317/41 (2013.01); Y02P 20/52 (2015.11)

(58) Field of Classification Search
None
See application file for complete search history.

(56) References Cited

U.S. PATENT DOCUMENTS

| 5,356,802 A | 10/1994 | Chandrasegaran |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,534,261 B1 | 3/2003 | Cox, III et al. |
| 6,607,882 B1 | 8/2003 | Cox, III et al. |
| 6,903,185 B2 | 6/2005 | Kim et al. |
| 7,153,949 B2 | 12/2006 | Kim et al. |
| 7,888,121 B2 | 2/2011 | Urnov et al. |
| 9,376,484 B2 * | 6/2016 | Lin .................... C12P 21/02 |
| 2010/0145032 A1 | 6/2010 | Laine et al. |
| 2010/0247570 A1 | 9/2010 | Rosenberg et al. |
| 2011/0016546 A1 | 1/2011 | Bedell et al. |
| 2011/0030072 A1 | 2/2011 | Weinstein et al. |
| 2013/0039991 A1 | 2/2013 | Varki et al. |
| 2013/0164329 A1 | 6/2013 | Rossomando et al. |
| 2013/0243744 A1 | 9/2013 | Betenbaugh |
| 2014/0349341 A1 | 11/2014 | Lin et al. |

FOREIGN PATENT DOCUMENTS

| GB | 2 338 237 A | 12/1999 |
| WO | 98/37186 A1 | 8/1998 |
| WO | 98/53057 A1 | 11/1998 |
| WO | 00/27878 A1 | 5/2000 |
| WO | 01/88197 A2 | 11/2001 |
| WO | 02/077227 A2 | 10/2002 |
| WO | 2007/014275 A2 | 2/2007 |
| WO | 2010033085 A1 | 3/2010 |
| WO | 2013/106515 A1 | 7/2013 |

OTHER PUBLICATIONS

Stanley et al.,"Selection and Characterization of Eight Phenotypically Distinct Lines of Lectin-Resistant Chinese Hamster Ovary Cells" 6 Cell 121-128 (1975).*
Ripka et al., Co-Transformation of Lec1 CHO Cells With N-Acetylglucosaminyltransferase 1 Activity and a Selectable Marker 42 Journal of Cellular Biochemistry (1990).*
Liu et al., "Generation of a Triple-Gene Knockout Mammalian Cell Line Using Engineered Zinc-Finger Nucleases" 106(1) Biotechnology and Bioengineering 97-105 (2010).*
Fan et al., "Improving the Efficiency of CHO Cell Line Generation Using Glutamine Synthetase Gene Knockout Cells" 109(4) Biotechnology and Bioengineering 1007-1015 (Nov. 8, 2011).*
Chen et al., "Five Lec1 CHO cell mutants have distinct Mgat1 gene mutations that encode truncated N-acetylglucosaminyltransferase I" 13(1) Glycobiology 43-50 (2003).*

(Continued)

Primary Examiner — Nancy J Leith
(74) Attorney, Agent, or Firm — Polsinelli PC

(57) ABSTRACT

The present invention provides cell lines deficient in mannosyl (alpha-1,3-)-glycoprotein beta-1,2-N-acetylglucosaminyltransferase I (Mgat1). Also provided are methods for producing the Mga1 deficient cell lines and methods for using the Mgat1 deficient cell lines for the production of recombinant proteins having simple glycoforms.

16 Claims, 12 Drawing Sheets

(56) References Cited

OTHER PUBLICATIONS

Barnes et al., "Advances in animal cell recombinant protein production: GS-NS0 expression system," Cytotechnology, 2000, pp. 109-123, vol. 32.
Beerli et al., "Engineering polydactyl zinc-finger transcription factors," Nature Biotechnology, 2002, pp. 135-141, vol. 20.
Belfort et al., "Homing endonucleases: keeping the house in order," Nucleic Acids Research, 1997, pp. 3379-3388, vol. 25, No. 17.
Betting et al., "Enhanced immune stimulation by a therapeutic lymphoma tumor antigen vaccine produced in insect cells involves mannose receptor targeting to antigen presenting cells," Vaccine, 2009, pp. 250-259, vol. 27, No. 2.
Bitinaite et al., "Fokl dimerization is required for DNA cleavage," PNAS, 1998, pp. 10570-10575, vol. 95.
Chen et al., "Five Lec1 CHO cell mutants have distinct Mgat1 gene mutations that encode truncated N-acetylglucosaminyltransferase I," Glycobiology, 2003, pp. 43-50, vol. 13, No. 1.
Choo et al., "Advances in zinc finger engineering," Curr. Opin. Struct. Biol., 2000, pp. 411-416, vol. 10.
Doyon et al., "Heritable Targeted Gene Disruption in Zebrafish Using Designed Zinc Finger Nucleases," Nat. Biotechnol., 2008, pp. 702-708, vol. 26, No. 6.
Goh et al., "RCA-I-resistant CHO mutant cells have dysfunctional GnT I and expression of normal GnT I in these mutants enhances sialylation of recombinant erythropoietin," Metabolic Engineering, 2010, pp. 360-368, vol. 12.
Gribskov et al., "Sigma factors from E. coli, B. subtilis, phage SP01, and phage T4 are homologous proteins," Nucleic Acids Research, 1986, pp. 6745-6763, vol. 14, No. 16.
Hoppe, "Recombinant glucocerebrosidase and Lyme disease vaccine Made by genetic engineering (No. 11 in a series of articles to promote a better understanding of the use of genetic engineering)," Journal of Biotechnology, 2000, pp. 259-263, vol. 76.
Hossler et al.,"Optimal and consistent protein glycosylation in mammalian cell culture," Glycobiology, 2009, pp. 936-949, vol. 19, No. 9.
International Search Report and Written Opinion from related International Application No. PCT/US2013/020947, dated Mar. 26, 2013; 9 pgs.
International Preliminary Report on Patentability from related International Application No. PCT/US2013/020947, dated Jul. 15, 2014; 7 pgs.
International Search Report and Written Opinion from related International Application No. PCT/US2015/018474, dated May 26, 2015; 11 pgs.
Isalan et al., "A rapid, generally applicable method to engineer zinc fingers illustrated by targeting the HIV-1 promoter," Nat. Biotechnol., 2001, pp. 656-660, vol. 19, No. 7.
Jenkins et al., "Getting the glycosylation right: Implications for the biotechnology industry," Nature Biotechnology, 1996, pp. 975-981, vol. 14.
Kanda et al., "Comparison of Cell Lines for Stable Production of Fucose-Negative Antibodies With Enhanced ADCC," Biotechnology and Bioengineering, 1996, pp. 680-688, vol. 94, No. 4.
Kim et al., "Chimeric restriction endonuclease," PNAS, 1994, pp. 883-887, vol. 91.
Kim et al., "Insertion and Deletion Mutants of Fokl Restriction Endonuclease*," The Journal of Biological Chemistry, 1994, pp. 31978-31982, vol. 269, No. 50.
Lam et al., "A Model Vaccine Exploiting Fungal Mannosylation to Increase Antigen Immunogenicity," The Journal of Immunology, 2005, pp. 7496-7503, vol. 175.
Li et al., "Functional domains in Fok I restriction endonuclease," PNAS, 1992, pp. 4275-4279, vol. 89.
Li et al., "Alteration of the cleavage distance of Fok I restriction endonuclease by insertion mutagenesis," PNAS, 1993, pp. 2764-2768, vol. 90.
Makkerh et al., "Comparative mutagenesis of nuclear localization signals reveals the importance of neutral and acidic amino acids," Current Biology, 1996, pp. 1025-1027, vol. 6, No. 8.

Mandell et al., "Zinc Finger Tools: custom DNA-binding domains for transcription factors and nucleases," Nucleic Acids Research, 2006, pp. W516-W523, vol. 34.
Pabo et al., "Design and Selection of Novel CYS2HIS2 Zinc Finger Proteins," Annu. Rev. Biochem., 2001, pp. 313-340, vol. 70.
Roberts et al., "REBASE: restriction enzymes and methyltransferases," Nucleic Acids Research, 2003, pp. 418-420, vol. 31, No. 1.
Sander et al., "Zinc Finger Targeter (ZiFiT): an engineered zinc finger/target site design tool," Nucleic Acids Research, 2007, pp. W599-W605, vol. 35.
Sanjana et al., "A transcription activator-like effector toolbox for genome engineering," Nature Protocols, 2012, pp. 171-192, vol. 7, No. 1.
Santiago et al., "Targeted gene knockout in mammalian cells by using engineered zinc-finger nucleases," PNAS, 2008, pp. 5809-5814, vol. 105, No. 15.
Segal et al., "Custom DNA-binding proteins come of age: polydactyl zinc-finger proteins," Curr. Opin. Biotechnol., 2001, pp. 632-637, vol. 12.
Sera et al., "Rational Design of Artificial Zinc-Finger Proteins Using a Nondegenerate Recognition Code Table," Biochemistry, 2002, pp. 7074-7081, vol. 41.
Smith et al., "Comparison of Biosequences," Advances in Applied Mathematics, 1981, pp. 482-489, vol. 2.
Stanley et al., "Selection and Characterization of Eight Phenotypically Distinct Lines of Lectin-Resistant Chinese Hamster Ovary Cells," Cell, 1975, pp. 121-128, vol. 6.
Tan et al., "Mannose receptor-mediated uptake of antigens strongly enhances HLA class II-restricted antigen presentation by cultured dendritic cells," Eur. J. Immunol., 1997, pp. 2426-2435, vol. 27.
Van Patten et al., "Effect of mannose chain length on targeting of glucocerebrosidase for enzyme replacement therapy of Gaucher disease," Glycobiology, 2007, pp. 467-478, vol. 17, No. 5.
Xu et al., "The genomic sequence of the Chinese hamster ovary (CHO)-K1 cell line," Nature Biotechnology, 2011, pp. 735-741, vol. 29, No. 8.
Yang, "Applications of a Novel CHO Glycosylation Mutant," Doctoral dissertation, Department of Biochemistry, National University of Singapore, Jan. 22, 2014 (Jan. 22, 2014), pp. 1-127.
Zhang et al., "Solution Structure of the E200K Variant of Human Prion Protein," The Journal of Biological Chemistry, 2000, pp. 33650-33654, vol. 275, No. 43.
Zhong et al., "Engineering Novel Lec1 Glycosylation Mutants in CHO-DUKX Cells: Molecular Insights and Effector Modulation of N-Acetylglucosaminyltransferase I," Biotechnology and Bioengineering, 2012, pp. 1723-1734, vol. 109, No. 7.
Zhou et al., "Development of a Simple and Rapid Method for Producing Non-Fucosylated Oligomannose Containing Antibodies With Increased Effector Function," Biotechnology and Bioengineering, 2008, pp. 652-665, vol. 99, No. 3.
Notice of Allowance from related U.S. Appl. No. 14/371,137, dated Feb. 26, 2016; 11 pgs.
Office Action from related U.S. Appl. No. 14/371,137, dated Jul. 10, 2015; 21 pgs.
Office Action from related U.S. Appl. No. 14/371,137, dated Feb. 26, 2015; 14 pgs.
Office Action from related Japanese Patent Application No. 2014-552284, dated Sep. 27, 2016; 10 pgs.
First Office Action and Search Report from related Chinese Patent Application No. 201380005345.X, dated Aug. 5, 2015; 12 pgs.
Second Office Action and Search Report from related Chinese Patent Application No. 201380005345.X, dated Apr. 11, 2016; 12 pgs.
Third Office Action from related Chinese Patent Application No. 201380005345.X, dated Oct. 31, 2016; 8 pgs.
First Exam Report from related European Application No. EP 13735783.6, dated Jun. 6, 2016; 5 pgs.
Supplementary European Search Report from related European Application No. EP 13735783.6, dated Oct. 5, 2015; 10 pgs.
Fan et al., "Improving the Efficiency of CHO Cell Line Generation Using Glutamine Synthetase Gene Knockout Cells," Biotechnology and Bioengineering, 2012, pp. 1007-1015, vol. 109, No. 4.

(56) References Cited

OTHER PUBLICATIONS

Liu et al., "Generation of a Triple-Gene Knockout Mammalian Cell Line Using Engineered Zinc-Finger Nucleases," Biotechnology and Bioengineering, 2010, pp. 97-105, vol. 106, No. 1.

Ripka et al., "Co-Transformation of Lec1 CHO Cells With N-Acetylglucosaminyltransferase 1 Activity and a Selectable Marker," Journal of Cellular Biochemistry, 1990, pp. 117-122, vol. 42.

Sealover et al., "Engineering Chinese Hamster Ovary (CHO) cells for producing recombinant proteins with simple glycoforms by zinc-finger nuclease (ZFN)-mediated gene knockout of mannosyl (alpha-1,3-)-glycoprotein beta-1,2-N-acetylglucosaminyltransferase (Mgat1)," Journal of Biotechnology, 2013, pp. 24-32, vol. 167, No. 1.

Wurm, "Production of recombinant protein therapeutics in cultivated mammalian cells," Nature Biotechnology, 2004, pp. 1393-1398, vol. 22, No. 11.

\* cited by examiner

FIG. 5

PRODUCTION OF RECOMBINANT PROTEINS WITH SIMPLE GLYCOFORMS

CROSS-REFERENCE TO RELATED APPLICATIONS

This application is a continuation application of U.S. patent application Ser. No. 14/371,137, filed Jul. 8, 2014, which is a U.S. National Stage Application of PCT International Application No. PCT/US2013/020947, filed Jan. 10, 2013, which claims the priority of U.S. Provisional Application Ser. No. 61/585,508, filed Jan. 11, 2012, U.S. Provisional Application Ser. No. 61/636,680, filed Apr. 22, 2012, and U.S. Provisional Application Ser. No. 61/720,268, filed Oct. 30, 2012, the disclosure of each is hereby incorporated by reference in its entirety.

FIELD OF THE INVENTION

The present invention relates to recombinant proteins with simple glycoforms. In particular, the present invention relates to compositions and methods for producing recombinant glycoproteins having one or more terminal mannose residues.

BACKGROUND OF THE INVENTION

N-linked glycosylation is a common protein modification found on many secreted and membrane-bound glycoproteins. The synthesis of complex glycoforms requires a series of enzymatic reactions carried out in a step-wise manner in the endoplasmic reticulum and Golgi apparatus of eukaryotic cells. While the majority of recombinant therapeutic proteins require the presence of complex glycans to avoid immunogenicity and to improve protein half-life, applications for glycoproteins with simple N-glycan structures also exist. For example, recombinant proteins with simple glycoforms are advantageous for X-ray crystallography studies. Additionally, simple glycoforms with only terminal mannose residues can lead to increased efficacy of some therapeutics by facilitating mannose receptor-mediated uptake for these proteins.

Most cell lines used for the production of therapeutic glycoproteins produce proteins with heterogeneous or complex N-linked glycoforms, however. Thus, there is a need for cell lines that are engineered to produce recombinant glycoproteins with simple glycoforms. Moreover, it is desirable that these engineered cell lines stably produce proteins with terminal mannose residues, while retaining high protein productivity and robust growth in chemically-defined culture media.

SUMMARY

Among the various aspects of the present disclosure is the provision of a cell line deficient in mannosyl (alpha-1,3-)-glycoprotein beta-1,2-N-acetylglucosaminyltransferase I (Mgat1), wherein the deficiency in Mgat1 is due to a deletion of less than 200 base pairs in the coding region of a chromosomal sequence encoding Mgat1. In one embodiment, the cell line comprises an insertion in addition to the deletion in the coding region of the chromosomal sequence encoding Mgat1. In some embodiments, the cell line deficient in Mgat1 produces no Mgat1 protein. In other embodiments, the cell line deficient in Mgat1 produces a reduced amount of Mgat1 protein relative to the parental cell line that is not deficient in Mgat1. In one embodiment, the Mgat1 deficient cell line comprises an inactivated chromosomal sequence encoding Mgat1. The chromosomal sequence encoding Mgat1 can be inactivated with a targeting endonuclease. In certain embodiments, the targeting endonuclease is selected from a zinc finger nuclease, a transcription activator-like effector nuclease (TALEN), a meganuclease, and a site-specific endonuclease. In one embodiment, the targeting endonuclease is a zinc finger nuclease. In some embodiments, the chromosomal sequence encoding Mgat1 is inactivated due to a deletion of at least one base pair, an insertion of at least one base pair, a substitution of at least one base pair, or combinations thereof. In certain embodiments, the chromosomal sequence encoding Mgat1 is inactivated due to a deletion 2-55 base pairs. In one embodiment the cell line deficient in Mgat1 is also deficient in glutamine synthetase (GS), dihydrofolate reductase (DHFR), hypoxanthine-guanine phosphoribosyltransferase (HPRT), or a combination thereof. In another embodiment, the Mgat1 deficient cell line is a CHO cell line. In one embodiment, the cell line deficient in Mgat1 is a CHO cell line in which the single copy of the chromosomal sequence encoding Mgat1 is inactivated by a deletion and the cell line produces no Mgat1. In another embodiment, the cell line deficient in Mgat1 is a CHO GS –/– cell line in which the single copy of the chromosomal sequence encoding Mgat1 is inactivated by a deletion and the cell line produces no Mgat1. In one embodiment, the Mgat1 deficient cell line expresses at least one glycoprotein having a simple glycoform, wherein the simple glycoform comprises one or more terminal mannose residues. In one embodiment, the Mgat1 deficient cell line has a growth rate comparable to a cell line having no deficiency in Mgat1. In one embodiment, the cell line deficient in Mgat1 produces a level of protein comparable to a cell line having no deficiency in Mgat1.

Another aspect of the disclosure encompasses a method for producing a cell deficient in Mgat1. The method comprises transfecting a host cell with a targeting endonuclease that targets a specific sequence in a chromosomal sequence encoding Mgat1. The targeting endonuclease can be a zinc finger nuclease, a transcription activator-like effector nuclease (TALEN), a meganuclease, or a site-specific endonuclease. In one embodiment the targeting endonuclease is a zinc finger nuclease. In one embodiment, the host cell is a mammalian cell. In another embodiment the host cell is also deficient in glutamine synthetase (GS), dihydrofolate reductase (DHFR), hypoxanthine-guanine phosphoribosyltransferase (HPRT), or a combination thereof. In one embodiment, the host cell is a CHO cell. In another embodiment, the host cell is a GS –/– CHO cell. In one embodiment, the transfected host cell is incubated with *Ricinus communis* agglutinin-I (RCA-I).

Still another aspect of the present disclosure is a method for producing a recombinant protein having one or more terminal mannose residues. The method comprises introducing a nucleic acid encoding the recombinant protein into a cell line in which all chromosomal sequences encoding Mgat1 are inactivated such that the cell line produces no Mgat1, and expressing the recombinant protein. In one embodiment, the chromosomal sequence encoding Mgat1 is inactivated by a targeting endonuclease chosen from a zinc finger nuclease, a transcription activator-like effector nuclease (TALEN), a meganuclease, and a site-specific endonuclease. In one embodiment, the targeting endonuclease is a zinc finger nuclease. In one embodiment, the inactivated chromosomal sequence encoding Mgat1 comprises a deletion of 2-55 base pairs. In one embodiment, the cell line that produces no Mgat1 is a CHO cell line. In another embodiment, the cell line that produces no Mgat1 is a GS −/− CHO cell line. In one embodiment, the expressed recombinant protein has a simple glycoform comprising one or more terminal mannose residues.

Other aspects and iterations of the disclosure are described in more detail below.

BRIEF DESCRIPTION OF THE DRAWINGS

FIG. 5 presents the genotypes of Mgat1 disrupted IgG producing clones. Shown is the sequence alignment of the following cell lines: non-transfected wildtype (wt); two wildtype clones (#15, #46) that underwent the ZFN transfection and clone isolation; two Mgat1 disrupted cell lines selected without RCA-I (#73, #92) and four Mgat1 disrupted cell lines selected in the presence of RCA-I (#21, #25, #27, #37). The shaded area marks the ZFN cut site.

DETAILED DESCRIPTION OF THE INVENTION

The present disclosure provides compositions and methods for the production of recombinant proteins having simple glycoforms, wherein a simple glycoform comprises one or more terminal mannose residues. In particular, the present disclosure provides cell lines deficient in mannosyl (alpha-1,3-)-glycoprotein beta-1,2-N-acetylglucosaminyltransferase I (Mgat1). In some embodiments, the Mgat1 deficient cell line comprises an inactivated or knocked-out chromosomal sequence encoding Mgat1 such that the cell line produces no Mgat1. As a consequence, the cell line produces glycoproteins having one or more terminal mannose residues. The Mgat1 deficient cell lines disclosed herein are useful for vaccine production because glycoproteins with terminal mannose residues facilitate mannose receptor-mediated uptake. Additionally, glycoproteins with simple glycoforms are useful for X-ray crystallography studies. Moreover, the Mgat1 deficient cells disclosed herein avoid potential regulatory concerns associated with random chemical mutagenesis and maintain growth and productivity characteristics that are comparable to those of the parental cell lines.

The present disclosure also provides methods for preparing the Mgat1 deficient cells. For example, the cells deficient in Mgat1 can be prepared by using targeting endonucleases to inactivate the chromosomal sequence(s) encoding Mgat1. Also provided are methods for producing recombinant glycoproteins with simple glycoforms using the Mgat1 deficient cells disclosed herein.

(I) Mgat1 Deficient Cell Lines (a) Properties of the Cell Line

Figure 1:
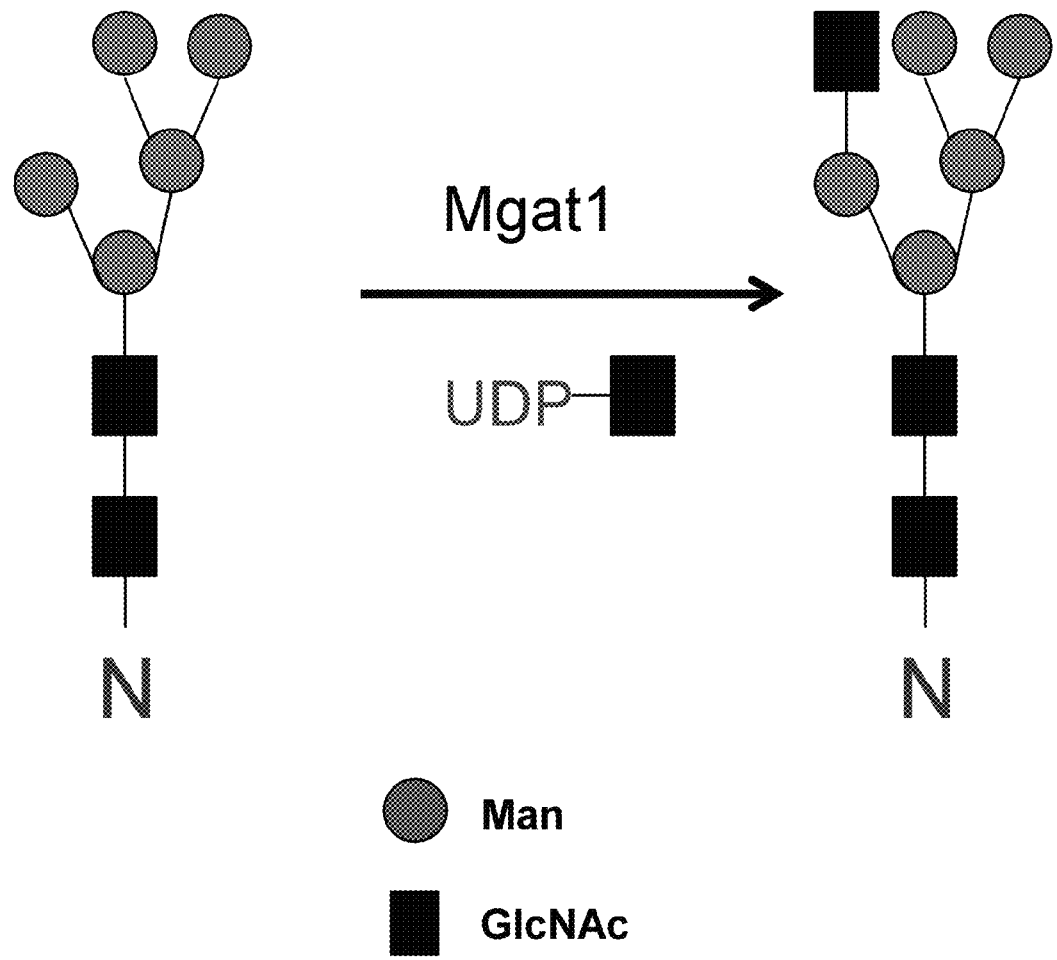
FIG. 1 is a schematic diagram showing the role of Mgat1 in N-glycan synthesis. Mgat1 catalyzes the transfer of a GlcNAc residue to a Man5GlcNAc2 (Man5) glycoform.

One aspect of the present disclosure encompasses cell lines deficient in Mgat1. Mgat1 is also known as N-acetylglucosaminyltransferase I (GlcAc-TI or GnTI) or N-glycosyl-oligosaccharide-glycoprotein N-acetylglucosaminyltransferase I. Mgat1 catalyzes the transfer of N-acetylglucosamine (GlcNAc) onto the oligomannose core (i.e., Man5GlcNAc2 (Man5) moiety) of a growing N-glycan (see FIG. 1).

In some embodiments, the Mgat1 deficient cell line has reduced levels of Mgat1 relative to the parental cell line. For example, the levels of Mgat1 in the Mgat1 deficient cell line can be reduced from about 5% to about 10%, from about 10% to about 20%, from about 20% to about 30%, from about 30% to about 40%, from about 40% to about 50%, from about 50% to about 60%, from about 60% to about 70%, from about 70% to about 80%, from about 80% to about 90%, or from about 90% to about 99.9% relative to the parental cell line that is not deficient in Mgat1. In other embodiments, the Mgat1 deficient cell line produces essentially no Mgat1. As used herein, the term "essentially no Mgat1" means that no Mgat1 mRNA and/or protein can be detected in the Mgat1 deficient cell lines or lysates derived therefrom using procedures well known in the art. Non-limiting examples of suitable procedures for determining the level of mRNA or protein include PCR, qPCR, Western blotting, and ELISA assays.

The cell lines deficient in Mgat1 produce glycoproteins with simple glycoforms. A simple glycoform refers to a glycoform comprising one or more terminal mannose residues. In general, a simple glycoform is devoid of galactose and/or sialic acid residues. An exemplary simple glycoform is Man5GlcNac2 or Man5. In some embodiments, the Mgat1 deficient cell lines can produce glycoproteins in which the levels of terminal mannose residues are increased from about 1.1-fold to about 3-fold, from about 3-fold to about 10-fold, from about 10-fold to about 30-fold, from about 30-fold to about 100-fold, or more than about 100-fold. In other embodiments, the Mgat1 deficient cell lines can produce glycoproteins in which the levels of terminal galactose and/or sialic acid residues are decreased from about 1.1-fold to about 3-fold, from about 3-fold to about 10-fold, from about 10-fold to about 30-fold, from about 30-fold to about 100-fold, or more than about 100-fold.

The Mgat1 deficient cell lines have levels of protein production or productivity that are comparable to those of cell lines that are not deficient in Mgat1. As used herein, "comparable protein production" means that the Mgat1 deficient cell lines produce about the same level or more protein than cell lines that are not deficient in Mgat1. Protein productivity can be quantified by determining the amount of protein produced per unit volume (i.e., peak volumetric productivity). In some embodiments, the amount of protein produced by the Mgat1 deficient cell lines can vary about ±10% relative to that produced by cell lines that are not deficient in Mgat1. In other embodiments, the amount of protein produced by the Mgat1 deficient cell lines can be increased from about 10% to about 20%, from about 20% to about 30%, from about 30% to about 40%, or from about 40% to about 50% relative to that produced by cell lines that are not deficient in Mgat1.

The Mgat1 deficient cell lines have growth rates that are comparable to those of cell lines that are not deficient in Mgat1. As used herein, "comparable growth rates" refer to growth rates that are either increased relative to cell lines that are not deficient in Mgat1 or decreased by less than about 50% relative to cell lines that are not deficient in Mgat1. Growth rates can be quantified by determining the percentage of viable cells or the number of viable cells per unit volume (i.e., viable cell density) after a certain period of time in culture. In some embodiments, the Mgat1 deficient cell lines have increased rates of growth relative to cell lines that are not deficient in Mgat1. For example, the percentage of viable cells or viable cell density in the Mgat1 deficient cell lines can be increased from about 1% to about 10%, from about 10% to about 30%, from about 30% to about 5%, from about 50% to about 100%, or more than 100% relative to cell lines that are not deficient in Mgat1. In other embodiments, the percentage of viable cells or viable cell density in the Mgat1 deficient cell lines can be decreased from about 1% to about 10%, from about 10% to about 30%, from about 30% to about 50% relative to cell lines that are not deficient in Mgat1.

The Mgat1 deficient cell lines disclosed herein have stable phenotypes. For example, the Mgat1 deficient cell lines produce glycoproteins with simple glycoforms for extended periods of time and/or over countless cell generations. Stated another way, the cell lines disclosed herein do not revert to producing glycoproteins with complex glycoforms. Additionally, the cell lines deficient in Mgat1 maintain high levels of protein productivity and excellent growth rates for extended periods of time and/or over innumerable cell generations.

(b) Inactivated Chromosomal Sequence Encoding Mgat1

In some embodiments, the cell line deficient in Mgat1 comprises an inactivated chromosomal sequence encoding Mgat1. For example, the genome of the cell line can be edited to inactivate the chromosomal sequence encoding Mgat1. As used herein, the term "inactivated chromosomal sequence" refers to a chromosomal sequence that is unable to generate a protein product. In embodiments in which the cell line comprises euploid cells, the inactivated chromosomal sequence encoding Mgat1 can be monoallelic such that the cell line produces reduced levels of Mgat1. In other embodiments in which the cell line comprises euploid cells, the inactivated chromosomal sequence encoding Mgat1 can be biallelic such that the cell line produces no Mgat1. In other embodiments in which the cell line is aneuploid, one or more copies of the chromosomal sequence(s) encoding Mgat1 can be inactivated such that the cell produces a reduced amount of Mgat1. In still other embodiments in which the cell line is aneuploid, all copies of the chromosomal sequence(s) encoding Mgat1 can be inactivated such that the cell line produces no Mgat1. In an exemplary embodiment, the cell line is haploid for the chromosomal sequence encoding Mgat1, and inactivation of the chromosomal sequence encoding Mgat1 results in a complete loss of Mgat1 expression.

The chromosomal sequence encoding Mgat1 can be inactivated by a deletion of at least one base pair (bp), an insertion of at least one bp, a substitution of at least one bp, or combinations thereof. As a consequence of the deletion(s) insertion(s), and/or substitution(s), the Mgat1 coding sequence undergoes a shift in the reading frame, thereby preventing production of a protein product. The chromosomal sequence encoding Mgat1 can be inactivated using targeting endonuclease-mediated genome editing technology as detailed below in section (II). In various embodiments, the chromosomal sequence encoding Mgat1 can be inactivated by deletion of all or part of the exonic coding region, deletion of all or part of a control region, and/or deletion of a splice site such that expression of Mgat1 is abolished. In other embodiments, the chromosomal sequence encoding Mgat1 can be inactivated via deletions, insertions, and/or nucleotide substitutions to introduce a premature stop codon, new splice sites, and/or SNPs into the chromosomal sequence such that the cell line is unable to produce Mgat1.

In one embodiment, the Mgat1 deficient cell line comprises a deletion ranging from about 1 bp to the entire coding region of the chromosomal sequence encoding Mgat1. In another embodiment, the Mgat1 deficient cell line comprises a deletion ranging from about 2 bp to about 55 bp, from about 55 bp to about 100 bp, from about 100 bp to about 300 bp, from about 300 bp to about 600 bp, from about 600 bp to about 1200 bp, or more than about 1200 bp of coding region of Mgat1. In exemplary embodiments, the Mgat1 deficient cell line comprises a deletion of 2 bp, 4 bp, 7 bp, 10, bp, 18 bp, 24 bp, 28 bp, or 55 bp of the chromosomal sequence encoding Mgat1. In another exemplary embodiment, the Mgat1 deficient cell line comprises a deletion of 157 bp that is replaced by an insertion of 104 bp of the chromosomal sequence encoding Mgat1.

(c) Optional Additional Deficiencies

In some embodiments, the Mgat1 deficient cell line also comprises a deficiency in glutamine synthetase (GS), dihydrofolate reductase (DHFR), hypoxanthine-guanine phosphoribosyltransferase (HPRT), or combinations thereof. The deficiency in GS, DHFR, and/or HPRT can be naturally occurring. Alternatively, the deficiency in GS, DHFR, and/or HPRT can be engineered. For example, the cell can be deficient in GS, DHFR, or HPRT because the cell comprises an inactivated chromosomal sequence encoding GS, DHFR, or HPRT, respectively. In some embodiments, the chromosomal sequence(s) encoding GS, DHFR, or HPRT can be inactivated by targeting endonuclease-mediated genome editing. In exemplary embodiments, all copies of the chromosomal sequence(s) encoding GS, DHFR, or HPRT are inactivated such that the cell lines produce no GS, DHFR, or HPRT, respectively. In an exemplary embodiment, the Mgat1 deficient cell line is GS −/−.

(d) Cell Line Types

The type of cell line that is deficient in Mgat1 can vary. The cell line can be a human cell line, a non-human mammalian cell line, a non-mammal vertebrate cell line, an invertebrate cell line, or a yeast cell line.

Non-limiting examples of suitable mammalian cell lines include Chinese hamster ovary (CHO) cells, baby hamster kidney (BHK) cells; mouse myeloma NSO cells, mouse embryonic fibroblast 3T3 cells (NIH3T3), mouse B lymphoma A20 cells; mouse melanoma B16 cells; mouse myoblast C2C12 cells; mouse myeloma SP2/0 cells; mouse embryonic mesenchymal C3H-10T1/2 cells; mouse carcinoma CT26 cells, mouse prostate DuCuP cells; mouse breast EMT6 cells; mouse hepatoma Hepa1c1c7 cells; mouse myeloma J5582 cells; mouse epithelial MTD-1A cells; mouse myocardial MyEnd cells; mouse renal RenCa cells; mouse pancreatic RIN-5F cells; mouse melanoma X64 cells; mouse lymphoma YAC-1 cells; rat glioblastoma 9L cells; rat B lymphoma RBL cells; rat neuroblastoma B35 cells; rat hepatoma cells (HTC); buffalo rat liver BRL 3A cells; canine kidney cells (MDCK); canine mammary (CMT) cells; rat osteosarcoma D17 cells; rat monocyte/macrophage DH82 cells; monkey kidney SV-40 transformed fibroblast (COS7) cells; monkey kidney CVI-76 cells; African green monkey kidney (VERO-76) cells; human embryonic kidney cells (HEK293, HEK293T); human cervical carcinoma cells (HELA); human lung cells (W138); human liver cells (Hep G2); human U2-OS osteosarcoma cells, human A549 cells, human A-431 cells, and human K562 cells. An extensive list of mammalian cell lines may be found in the American Type Culture Collection catalog (ATCC, Mamassas, Va.)

Examples of suitable non-mammalian cell lines include but are not limited to *Xenopus* cell lines (such as S3, XTC, BB7, ff-2, 15/0, and 15/40); zebrafish cell lines (such as, ZF4, PAC2 etc.); insect cell lines (such as SF9, S2, and the like); and yeast cell lines such as *Pichia* cell lines and *Saccharomyces* cell lines.

In exemplary embodiments, the cell line is a type that is widely used for the production of recombinant proteins, such as antibodies, glycoproteins, and the like. In exemplary embodiments, the cell line is a CHO cell line. Numerous CHO cell lines are available from ATCC. Suitable CHO cell lines include, but are not limited to, CHO-K1 cells and derivatives thereof.

(e) Optional Nucleic Acid

In some embodiments, the Mgat1 deficient cell line may further comprise at least one nucleic acid sequence encoding a recombinant protein. In general, the recombinant protein is heterologous, meaning that the protein is not native to the cell. The recombinant protein may be, without limit, an antibody, a fragment of an antibody, a monoclonal antibody, a humanized antibody, a humanized monoclonal antibody, a chimeric antibody, an IgG molecule, an IgG heavy chain, an IgG light chain, an IgA molecule, an IgD molecule, an IgE molecule, an IgM molecule, a vaccine, a growth factor, a cytokine, an interferon, an interleukin, a hormone, a clotting (or coagulation) factor, a blood component, an enzyme, a therapeutic protein, a nutraceutical protein, a functional fragment or functional variant of any of the forgoing, or a fusion protein comprising any of the foregoing proteins and/or functional fragments or variants thereof.

In some embodiments, the nucleic acid sequence encoding the recombinant protein may be linked to a nucleic acid sequence encoding hypoxanthine-guanine phosphoribosyltransferase (HPRT), dihydrofolate reductase (DHFR), and/or glutamine synthetase (GS), such that HPRT, DHFR, and/or GS may be used as an amplifiable selectable marker.

In some embodiments, the nucleic acid sequence encoding the recombinant protein may be extrachromosomal. That is, the nucleic acid encoding the recombinant protein may be transiently expressed from a plasmid, a cosmid, an artificial chromosome, a minichromosome, or another extrachromsomal construct. The expression construct can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. Additional information can be found in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., 3rd edition, 2001.

In other embodiments, the nucleic acid sequence encoding the recombinant protein may be chromosomally integrated into the genome of the cell. Accordingly, the recombinant protein can be stably expressed. In some iterations of this embodiment, the nucleic acid sequence encoding the recombinant protein may be operably linked to an appropriate heterologous expression control sequence (i.e., promoter). In other iterations, the nucleic acid sequence encoding the recombinant protein may be placed under control of an endogenous expression control sequence. The nucleic acid sequence encoding the recombinant protein can be integrated into the genome of the cell line using homologous recombination, targeting endonuclease-mediated genome editing, viral vectors, transposons, plasmids, and other well known means. Additional guidance can be found in Ausubel et al. 2003, supra and Sambrook & Russell, 2001, supra.

(f) Exemplary Embodiments

In one exemplary embodiment, the cell line is a CHO cell line in which the single copy of the chromosomal sequence encoding Mgat1 is inactivated (i.e., the genotype of the cell is Mgat1 −/0). In another exemplary embodiment, the cell line is a GS −/− CHO cell line in which the single copy of the chromosomal sequence encoding Mgat1 is inactivated (i.e., the genotype of the cell is GS −/−, Mgat1 −/0). In general, the chromosomal sequence encoding Mgat1 is inactivated by a deletion of part of the coding sequence.

(II) Methods for Preparing Cell Lines Deficient in Mgat1

The cell lines deficient in Mgat1 can be prepared by a variety of methods. In certain embodiments, the Mgat1 deficient cell line can be prepared by a targeting endonuclease-mediated genome editing process. In other embodiments, the Mgat1 deficient cell line can be prepared by RNAi methods, random mutagenesis, site-specific recombination systems, or other methods known in the art.

The cell lines deficient in Mgat1 produce glycoproteins having one or more terminal mannose residues. In additional embodiments, the Mgat1 deficient cell lines can be further enriched by incubation with *Ricinus communis* agglutinin-I (RCA-I). RCA-I is a cytotoxic lectin that does not bind terminal mannose residues and therefore allows for the selection of cells devoid of Mgat1 activity because such cells produce glycoproteins with terminal mannose residues.

(a) Targeting Endonuclease-Mediated Genome Editing

Targeting endonucleases can be used to edit (i.e., inactivate or modify) a specific chromosomal sequence. A specific chromosomal sequence can be inactivated by introducing into a cell a targeting endonuclease or a nucleic acid encoding the targeting endonuclease, which is engineered to target a specific chromosomal sequence. In one embodiment, the targeting endonuclease recognizes and binds the specific chromosomal sequence and introduces a double-stranded break that is repaired by a non-homologous end-joining (NHEJ) repair process. Because NHEJ is error prone, a deletion, insertion, and/or substitution of at least one nucleotide may occur, thereby disrupting the reading frame of the chromosomal sequence such that no protein product is produced. In another embodiment, the targeting endonucleases can also be used to edit a chromosomal sequence via a homologous recombination reaction by co-introducing a polynucleotide having substantial sequence identity with a portion of the targeted chromosomal sequence. The double-stranded break introduced by the targeting endonuclease is repaired by a homology-directed repair process such that the chromosomal sequence is exchanged with the polynucleotide in a manner that results in the chromosomal sequence being edited.

(i) Targeting Endonucleases

A variety of targeting endonucleases can be used to edit the chromosomal sequence. The targeting endonuclease can be a naturally-occurring protein or an engineered protein. In one embodiment, the targeting endonuclease can be a meganuclease. Meganucleases are endodeoxyribonucleases characterized by long recognition sequences, i.e., the recognition sequence generally ranges from about 12 base pairs to about 40 base pairs. As a consequence of this requirement, the recognition sequence generally occurs only once in any given genome. Among meganucleases, the family of homing endonucleases named LAGLIDADG has become a valuable tool for the study of genomes and genome engineering. A meganuclease can be targeted to a specific chromosomal sequence by modifying its recognition sequence using techniques well known to those skilled in the art.

In another embodiment, the targeting endonuclease can be a transcription activator-like effector (TALE) nuclease. TALEs are transcription factors from the plant pathogen *Xanthomonas* that can be readily engineered to bind new DNA targets. TALEs or truncated versions thereof may be linked to the catalytic domain of endonucleases such as FokI to create targeting endonuclease called TALE nucleases or TALENs (Sanjana et al., 2012, Nat Protoc, 7(1):171-192).

In still another embodiment, the targeting endonuclease can be a site-specific endonuclease. In particular, the site-specific endonuclease can be a "rare-cutter" endonuclease whose recognition sequence occurs rarely in a genome. Generally, the recognition sequence of the site-specific endonuclease occurs only once in a genome. In an alternate further embodiment, the targeting endonuclease can be an artificial targeted DNA double strand break inducing agent.

In exemplary embodiments, the targeting endonuclease can be a zinc finger nuclease (ZFN). Typically, a ZFN comprises a DNA binding domain (i.e., zinc fingers) and a cleavage domain (i.e., nuclease), both of which are described below.

Zinc finger binding domain. Zinc finger binding domains can be engineered to recognize and bind to any nucleic acid sequence of choice. See, for example, Beerli et al. (2002) Nat. Biotechnol. 20:135-141; Pabo et al. (2001) Ann. Rev. Biochem. 70:313-340; Isalan et al. (2001) Nat. Biotechnol. 19:656-660; Segal et al. (2001) Curr. Opin. Biotechnol. 12:632-637; Choo et al. (2000) Curr. Opin. Struct. Biol. 10:411-416; Zhang et al. (2000) J. Biol. Chem. 275(43): 33850-33860; Doyon et al. (2008) Nat. Biotechnol. 26:702-708; and Santiago et al. (2008) Proc. Natl. Acad. Sci. USA 105:5809-5814. An engineered zinc finger binding domain may have a novel binding specificity compared to a naturally-occurring zinc finger protein. Engineering methods include, but are not limited to, rational design and various types of selection. Rational design includes, for example, using databases comprising doublet, triplet, and/or quadruplet nucleotide sequences and individual zinc finger amino acid sequences, in which each doublet, triplet or quadruplet nucleotide sequence is associated with one or more amino acid sequences of zinc fingers which bind the particular triplet or quadruplet sequence. See, for example, U.S. Pat. Nos. 6,453,242 and 6,534,261, the disclosures of which are incorporated by reference herein in their entireties. As an example, the algorithm of described in U.S. Pat. No. 6,453,242 can be used to design a zinc finger binding domain to target a preselected sequence. Alternative methods, such as rational design using a nondegenerate recognition code table may also be used to design a zinc finger binding domain to target a specific sequence (Sera et al. (2002) Biochemistry 41:7074-7081). Publically available web-based tools for identifying potential target sites in DNA sequences as well as designing zinc finger binding domains are known in the art. For example, tools for identifying potential target sites in DNA sequences can be found at zincfingertools.org. Tools for designing zinc finger binding domains can be found at zifit.partners.org/ZiFiT. (See also, Mandell et al. (2006) Nuc. Acid Res. 34:W516-W523; Sander et al. (2007) Nuc. Acid Res. 35:W599-W605.)

A zinc finger binding domain can be designed to recognize and bind a DNA sequence ranging from about 3 nucleotides to about 21 nucleotides in length. In one embodiment, the zinc finger binding domain can be designed to recognize and bind a DNA sequence ranging from about 9 to about 18 nucleotides in length. In general, the zinc finger binding domains of the zinc finger nucleases used herein comprise at least three zinc finger recognition regions or zinc fingers, wherein each zinc finger binds 3 nucleotides. In one embodiment, the zinc finger binding domain comprises four zinc finger recognition regions. In another embodiment, the zinc finger binding domain comprises five zinc finger recognition regions. In still another embodiment, the zinc finger binding domain comprises six zinc finger recognition regions. A zinc finger binding domain can be designed to bind to any suitable target DNA sequence. See for example, U.S. Pat. Nos. 6,607,882; 6,534,261 and 6,453,242, the disclosures of which are incorporated by reference herein in their entireties.

Exemplary methods of selecting a zinc finger recognition region include phage display and two-hybrid systems, which are described in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237, each of which is incorporated by reference herein in its entirety. In addition, enhancement of binding specificity for zinc finger binding domains has been described, for example, in WO 02/077227, the entire disclosure of which is incorporated herein by reference.

Zinc finger binding domains and methods for design and construction of fusion proteins (and polynucleotides encoding same) are known to those of skill in the art and are described in detail in, for example, U.S. Pat. No. 7,888,121, which is incorporated by reference herein in its entirety. Zinc finger recognition regions and/or multi-fingered zinc finger proteins can be linked together using suitable linker sequences, including for example, linkers of five or more amino acids in length. See, U.S. Pat. Nos. 6,479,626; 6,903,185; and 7,153,949, the disclosures of which are incorporated by reference herein in their entireties, for non-limiting examples of linker sequences of six or more amino acids in length. The zinc finger binding domain described herein may include a combination of suitable linkers between the individual zinc fingers of the protein.

In some embodiments, the zinc finger nuclease further comprises a nuclear localization signal or sequence (NLS). A NLS is an amino acid sequence which facilitates targeting the zinc finger nuclease protein into the nucleus to introduce a double stranded break at the target sequence in the chromosome. Nuclear localization signals are known in the art. See, for example, Makkerh et al. (1996) Current Biology 6:1025-1027.

Cleavage domain. A zinc finger nuclease also includes a cleavage domain. The cleavage domain portion of the zinc finger nuclease can be obtained from any endonuclease or exonuclease. Non-limiting examples of endonucleases from which a cleavage domain can be derived include, but are not limited to, restriction endonucleases and homing endonucleases. See, for example, New England Biolabs Catalog or Belfort et al. (1997) Nucleic Acids Res. 25:3379-3388. Additional enzymes that cleave DNA are known (e.g., S1 Nuclease; mung bean nuclease; pancreatic DNase I; micrococcal nuclease; yeast HO endonuclease). See also Linn et al. (eds.) Nucleases, Cold Spring Harbor Laboratory Press, 1993. One or more of these enzymes (or functional fragments thereof) can be used as a source of cleavage domains.

A cleavage domain also can be derived from an enzyme or portion thereof, as described above, that requires dimerization for cleavage activity. Two zinc finger nucleases can be required for cleavage, as each nuclease comprises a monomer of the active enzyme dimer. Alternatively, a single zinc finger nuclease can comprise both monomers to create an active enzyme dimer. As used herein, an "active enzyme dimer" is an enzyme dimer capable of cleaving a nucleic acid molecule. The two cleavage monomers can be derived from the same endonuclease (or functional fragments thereof), or each monomer can be derived from a different endonuclease (or functional fragments thereof).

When two cleavage monomers are used to form an active enzyme dimer, the recognition sites for the two zinc finger nucleases are preferably disposed such that binding of the two zinc finger nucleases to their respective recognition sites places the cleavage monomers in a spatial orientation to each other that allows the cleavage monomers to form an active enzyme dimer, e.g., by dimerizing. As a result, the near edges of the recognition sites can be separated by about 5 to about 18 nucleotides. For instance, the near edges can be separated by about 5, 6, 7, 8, 9, 10, 11, 12, 13, 14, 15, 16, 17 or 18 nucleotides. It will however be understood that any integral number of nucleotides or nucleotide pairs can intervene between two recognition sites (e.g., from about 2 to about 50 nucleotide pairs or more). The near edges of the recognition sites of the zinc finger nucleases, such as for example those described in detail herein, can be separated by 6 nucleotides. In general, the site of cleavage lies between the recognition sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31978-31982. Thus, a zinc finger nuclease can comprise the cleavage domain from at least one Type IIS restriction enzyme and one or more zinc finger binding domains, which may or may not be engineered. Exemplary Type IIS restriction enzymes are described for example in International Publication WO 07/014,275, the disclosure of which is incorporated by reference herein in its entirety. Additional restriction enzymes also contain separable binding and cleavage domains, and these also are contemplated by the present disclosure. See, for example, Roberts et al. (2003) Nucleic Acids Res. 31:418-420.

An exemplary Type IIS restriction enzyme, whose cleavage domain is separable from the binding domain, is FokI. This particular enzyme is active as a dimer (Bitinaite et al. (1998) Proc. Natl. Acad. Sci. USA 95: 10, 570-10, 575). Accordingly, for the purposes of the present disclosure, the portion of the FokI enzyme used in a zinc finger nuclease is considered a cleavage monomer. Thus, for targeted double-stranded cleavage using a FokI cleavage domain, two zinc finger nucleases, each comprising a FokI cleavage monomer, can be used to reconstitute an active enzyme dimer. Alternatively, a single polypeptide molecule containing a zinc finger binding domain and two FokI cleavage monomers can also be used.

In certain embodiments, the cleavage domain comprises one or more engineered cleavage monomers that minimize or prevent homodimerization. By way of non-limiting example, amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains. Exemplary engineered cleavage monomers of FokI that form obligate heterodimers include a pair in which a first cleavage monomer includes mutations at amino acid residue positions 490 and 538 of FokI and a second cleavage monomer that includes mutations at amino-acid residue positions 486 and 499.

Thus, in one embodiment of the engineered cleavage monomers, a mutation at amino acid position 490 replaces Glu (E) with Lys (K); a mutation at amino acid residue 538 replaces Iso (I) with Lys (K); a mutation at amino acid residue 486 replaces Gln (Q) with Glu (E); and a mutation at position 499 replaces Iso (I) with Lys (K). Specifically, the engineered cleavage monomers can be prepared by mutating positions 490 from E to K and 538 from I to K in one cleavage monomer to produce an engineered cleavage monomer designated "E490K:I538K" and by mutating positions 486 from Q to E and 499 from I to K in another cleavage monomer to produce an engineered cleavage monomer designated "Q486E:I499K." The above described engineered cleavage monomers are obligate heterodimer mutants in which aberrant cleavage is minimized or abolished. Engineered cleavage monomers can be prepared using a suitable method, for example, by site-directed mutagenesis of wild-type cleavage monomers (FokI) as described in U.S. Pat. No. 7,888,121, which is incorporated herein in its entirety.

(ii) Optional Polynucleotide

In some embodiments, the method for targeted genome editing further comprises introducing into the cell at least one polynucleotide comprising a sequence having substantial sequence identity to a sequence on at least one side of the targeted cleavage site. For example, the polynucleotide may comprise a first sequence having substantial sequence identity to sequence on one side of the targeted cleavage site and a second sequence having substantial sequence identity to sequence on the other side of the targeted cleavage site. Alternatively, the polynucleotide may comprise a first sequence having substantial sequence identity to sequence on one side of the targeted cleavage site and a second sequence having substantial sequence identity to a sequence located away from the targeted cleavage site. The sequence located away from the targeted cleavage site may be tens, hundreds, or thousands of nucleotides upstream or downstream of the targeted cleavage site.

The lengths of the first and second sequences in the polynucleotide that have substantial sequence identity to sequences in the chromosomal sequence can and will vary. In general, each of the first and second sequences in the polynucleotide is at least about 10 nucleotides in length. In various embodiments, the polynucleotide sequences having substantial sequence identity with chromosomal sequences can range from about 10 to 30 nucleotides, from about 30 to about 100 nucleotides, from about 100 to about 300 nucleotides, from about 300 to about 1000 nucleotides, from about 1000 to about 3000 nucleotides, or more than 3000 in length.

The phrase "substantial sequence identity" means that the sequences in the polynucleotide have at least about 75% sequence identity with the chromosomal sequences of interest. For example, at least one of the sequences in the polynucleotide can be identical to the targeted chromosomal sequence except that it contains a deletion, insertion, and/or substitution of at least one nucleotide such that, upon homologous recombination, an altered sequence is introduced into the chromosomal sequence. In various embodiments, the sequences in the polynucleotide can have about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% A sequence identity with the chromosomal sequence of interest.

In alternate embodiments, the polynucleotide can comprise an additional sequence that is flanked by the sequences having substantial sequence identity with the chromosomal sequence. Upon homologous recombination, the additional sequence can be integrated into the chromosomal sequence, thereby inactivating the chromosomal sequence and/or modifying the chromosomal sequence.

The length of the polynucleotide can and will vary. For example, the polynucleotide can range from about 20 nucleotides in length up to about 200,000 nucleotides in length. In various embodiments, the polynucleotide ranges from about 20 nucleotides to about 100 nucleotides in length, from about 100 nucleotides to about 1000 nucleotides in length, from about 1000 nucleotides to about 10,000 nucleotides in length, from about 10,000 nucleotides to about 100,000 nucleotides in length, or from about 100,000 nucleotides to about 200,000 nucleotides in length.

Typically, the polynucleotide will be DNA. The DNA can be single-stranded or double-stranded. The donor polynucleotide can be a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer.

In some embodiments, the polynucleotide can further comprise a marker. Non-limiting examples of suitable markers include restriction sites, fluorescent proteins, or selectable markers. Such markers enable screening for targeted integrations.

(iii) Introducing into the Cell

The targeting endonuclease can be introduced into the cell as a protein or as a nucleic acid that encodes the targeting endonuclease. The nucleic acid encoding the targeting endonuclease may be DNA or RNA (i.e., mRNA). In embodiments in which the encoding nucleic acid is mRNA, the mRNA may be 5' capped and/or 3' polyadenylated. In embodiments in which the encoding nucleic acid is DNA, the DNA can be linear or circular. The DNA can be part of a vector, wherein the encoding DNA is optionally operably linked to a suitable promoter. Additional information regarding appropriate vectors, promoters, other control elements, and means of introducing the vector into the cell can be found, for example, in Ausubel et al, 2003, supra and/or Sambrook & Russell, 2001, supra.

The targeting endonuclease or nucleic acid encoding the targeting endonuclease and the optional polynucleotide described above can be introduced into the cell by a variety of means. Suitable delivery means include microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In certain embodiments, the targeting endonuclease molecule and optional polynucleotides are introduced into a cell by nucleofection or electroporation.

In embodiments in which more than one targeting endonuclease molecule and more than one polynucleotide are introduced into a cell, the molecules can be introduced simultaneously or sequentially. For example, targeting endonuclease molecules, each specific for a targeted cleavage site (and optional polynucleotides) can be introduced at the same time. Alternatively, each targeting endonuclease molecule, as well as the optional polynucleotides(s) can be introduced sequentially.

The ratio of the targeting endonuclease (or encoding nucleic acid) molecule to the optional polynucleotide can and will vary. In general, the ratio of targeting endonuclease molecule to polynucleotide can range from about 1:10 to about 10:1. In various embodiments, the ratio of the targeting endonuclease molecule to polynucleotide is about 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, or 10:1. In one embodiment, the ratio is about 1:1.

(iv) Exemplary Embodiments

In some embodiments, the cell line deficient in Mgat1 is prepared by engineering a zinc finger nuclease (ZFN) to cleave a specific sequence in the Mgat1 gene. Upon introduction of the ZFN or nucleic acid encoding the ZFN into the parental cell line, the ZFN binds to and cleaves the specific sequence in the Mgat1 gene. The error prone NHEJ process repairs the double stranded break in the Mgat1 gene, thereby introducing a deletion, insertion, and/or substitution of at least one bp such that the Mgat1 gene is inactivated. In general, a region of the Mgat1 coding sequence is deleted such that the reading frame is disrupted and no Mgat1 protein is produced by the cell line deficient in Mgat1. In some embodiments, the Mgat1 deficient cell line generated via ZFN-mediated genome editing is further enriched by selection in the presence of RCA-I. In some embodiments, the Mgat1 deficient cell line is prepared by contacting a CHO cell line with a ZFN targeted to Mgat1. In some instances, the CHO cell line is GS −/−.

(b) RNA Interference

In another embodiment, the Mgat1 deficient cell line can be prepared using an RNA interference (RNAi) agent that inhibits expression of a target mRNA or transcript. The RNAi agent can lead to cleavage of the target mRNA or transcript. Alternatively, the RNAi agent can prevent or disrupt translation of the target mRNA into protein.

In some embodiments, the RNAi agent can be a short interfering RNA (siRNA). In general, a siRNA comprises a double-stranded RNA molecule that ranges from about 15 to about 29 nucleotides in length. The siRNA can be about 16-18, 17-19, 21-23, 24-27, or 27-29 nucleotides in length. In a specific embodiment, the siRNA is about 21 nucleotides in length. The siRNA can optionally further comprise one or two single-stranded overhangs, e.g., a 3' overhang on one or both ends. The siRNA can be formed from two RNA molecules that hybridize together or, alternatively, can be generated from a short hairpin RNA (shRNA) (see below). In some embodiments, the two strands of the siRNA are completely complementary, such that no mismatches or bulges exist in the duplex formed between the two sequences. In other embodiments, the two strands of the siRNA are substantially complementary, such that one or more mismatches and/or bulges may exist in the duplex formed between the two sequences. In certain embodiments, one or both of the 5' ends of the siRNA have a phosphate group, while in other embodiments one or both of the 5' ends lack a phosphate group. In other embodiments, one or both of the 3' ends of the siRNA have a hydroxyl group, while in other embodiments one or both of the 5' ends lack a hydroxyl group.

One strand of the siRNA, which is referred to as the "antisense strand" or "guide strand," includes a portion that hybridizes with the target transcript. In certain embodiments, the antisense strand of the siRNA is completely complementary with a region of the target transcript, i.e., it hybridizes to the target transcript without a single mismatch or bulge over a target region between about 15 and about 29 nucleotides in length, preferably at least 16 nucleotides in length, and more preferably about 18-20 nucleotides in length. In other embodiments, the antisense strand is substantially complementary to the target region, i.e., one or more mismatches and/or bulges may exist in the duplex formed by the antisense strand and the target transcript. Typically, siRNAs are targeted to exonic sequences of the target transcript. Those of skill in the art are familiar with programs, algorithms, and/or commercial services that design siRNAs for target transcripts. An exemplary example is the Rosetta siRNA Design Algorithm (Rosetta Inpharmatics, North Seattle, Wash.) and MISSION® siRNA (Sigma-Aldrich, St. Louis, Mo.). The siRNA can be enzymatically synthesized in vitro using methods well known to those of skill in the art. Alternatively, the siRNA can be chemically synthesized using oligonucleotide synthesis techniques that are well known in the art.

In other embodiments, the RNAi agent can be a short hairpin RNA (shRNA). In general, a shRNA is an RNA molecule comprising at least two complementary portions that are hybridized or are capable of hybridizing to form a double-stranded structure sufficiently long to mediate RNA interference (as described above), and at least one single-stranded portion that forms a loop connecting the regions of the shRNA that form the duplex. The structure is also called a stem-loop structure, with the stem being the duplex portion. In some embodiments, the duplex portion of the structure is completely complementary, such that no mismatches or bulges exist in the duplex region of the shRNA. In other embodiments, the duplex portion of the structure is substantially complementary, such that one or more mismatches and/or bulges exist in the duplex portion of the shRNA. The loop of the structure can be from about 1 to about 20 nucleotides in length, preferably from about 4 to about 10 about nucleotides in length, and more preferably from about 6 to about 9 nucleotides in length. The loop can be located at either the 5' or 3' end of the region that is complementary to the target transcript (i.e., the antisense portion of the shRNA).

The shRNA can further comprise an overhang on the 5' or 3' end. The optional overhang can be from about 1 to about 20 nucleotides in length, and more preferably from about 2 to about 15 nucleotides in length. In some embodiments, the overhang comprises one or more U residues, e.g., between about 1 and about 5 U residues. In some embodiments, the 5' end of the shRNA has a phosphate group, while in other embodiments it does not. In other embodiments, the 3' end of the shRNA has a hydroxyl group, while in other embodiments it does not. In general, shRNAs are processed into siRNAs by the conserved cellular RNAi machinery. Thus, shRNAs are precursors of siRNAs and are similarly capable of inhibiting expression of a target transcript that is complementary to a portion of the shRNA (i.e., the antisense portion of the shRNA). Those of skill in the art are familiar with the available resources (as detailed above) for the design and synthesis of shRNAs. An exemplary example is MISSION® shRNAs (Sigma-Aldrich).

In still other embodiments, the RNAi agent can be an RNAi expression vector. Typically, an RNAi expression vector is used for intracellular (in vivo) synthesis of RNAi agents, such as siRNAs or shRNAs. In one embodiment, two separate, complementary siRNA strands are transcribed using a single vector containing two promoters, each of which directs transcription of a single siRNA strand (i.e., each promoter is operably linked to a template for the siRNA so that transcription may occur). The two promoters can be in the same orientation, in which case each is operably linked to a template for one of the complementary siRNA strands. Alternatively, the two promoters can be in opposite orientations, flanking a single template so that transcription for the promoters results in synthesis of two complementary siRNA strands. In another embodiment, the RNAi expression vector can contain a promoter that drives transcription of a single RNA molecule comprising two complementary regions, such that the transcript forms a shRNA.

Those of skill in the art will appreciate that it is preferable for siRNA and shRNA agents to be produced in vivo via the transcription of more than one transcription unit. Generally speaking, the promoters utilized to direct in vivo expression of the one or more siRNA or shRNA transcription units may be promoters for RNA polymerase III (Pol III). Certain Pol III promoters, such as U6 or H1 promoters, do not require cis-acting regulatory elements within the transcribed region, and thus, are preferred in certain embodiments. In other embodiments, promoters for Pol II can be used to drive expression of the one or more siRNA or shRNA transcription units. In some embodiments, tissue-specific, cell-specific, or inducible Pol II promoters can be used.

A construct that provides a template for the synthesis of siRNA or shRNA can be produced using standard recombinant DNA methods and inserted into any of a wide variety of different vectors suitable for expression in eukaryotic cells. Recombinant DNA techniques are described in Ausubel et al, 2003, supra and Sambrook & Russell, 2001, supra. Those of skill in the art also appreciate that vectors can comprise additional regulatory sequences (e.g., termination sequence, translational control sequence, etc.), as well selectable marker sequences. DNA plasmids are known in the art, including those based on pBR322, PUC, and so forth. Since many expression vectors already contain a suitable promoter or promoters, it may be only necessary to insert the nucleic acid sequence that encodes the RNAi agent of interest at an appropriate location with respect to the promoter(s). Viral vectors can also be used to provide intracellular expression of RNAi agents. Suitable viral vectors include retroviral vectors, lentiviral vectors, adenoviral vectors, adeno-associated virus vectors, herpes virus vectors, and so forth. In a specific embodiment, the RNAi expression vector is a shRNA lentiviral-based vector or lentiviral particle, such as that provided in MISSION® TRC shRNA products (Sigma-Aldrich).

The RNAi agents or RNAi expression vectors can be introduced into the cell using methods well known to those of skill in the art. Such techniques are described in Ausubel et al., 2003, supra or Sambrook & Russell, 2001, supra, for example. In certain embodiments, the RNAi expression vector, e.g., a viral vector, is stably integrated into the genome of the cell, such that Mgat1 expression is disrupted over subsequent cell generations.

(c) Site-Specific Recombination

In alternate embodiments, the Mgat1 deficient cell line can be prepared using site-specific recombination techniques. For example, site-specific recombination techniques can be used to delete all or part of a chromosomal sequence of interest, or introduce single nucleotide polymorphisms (SNPs) into the chromosomal sequence of interest. In one embodiment, the chromosomal sequence of interest is targeted using a Cre-loxP site-specific recombination system, a Flp-FRT site-specific recombination system, or variants thereof. Such recombination systems are commercially available, and additional teaching for these techniques is found in Ausubel et al., 2003, supra, for example.

(III) Methods for Producing Recombinant Proteins with Simple Glycoforms

Also provided are methods for using the Mgat1 deficient cells to produce recombinant proteins with simple glycoforms. A simple glycoform refers to a glycoform comprising one or more terminal mannose residues. In general, a simple glycoform is devoid of galactose and/or sialic acid residues. An exemplary simple glycoform is Man5GlcNac2 or Man5. As mentioned above, glycoproteins with simple glycoforms are useful for X-ray crystallography studies. Glycoproteins with simple glycoforms have additional applications. For example, the Mgat1 deficient cells can be used for vaccine production. The Mgat1 deficient cells produce glycoproteins containing terminal mannose residues. The terminal mannose residues on the antigen allow for its uptake by mannose receptors on antigen presenting cells. The antigen presenting cells (i.e., macrophages or dendritic cells) then present the antigen for recognition by T cells, thereby mounting an immune response. Use of antigens comprising terminal mannose residues can enhance the efficiency of antigen presentation to T cells. Additionally, glycoproteins with only terminal mannose residues may be useful for other therapeutic purposes by facilitating mannose receptor-mediated uptake of these proteins.

Glycoproteins with simple glycoforms can be prepared A further aspect of the present disclosure encompasses a method for producing a recombination protein with a simple glycoform. The method comprises introducing a nucleic acid encoding the recombinant protein into a cell line deficient in Mgat1 and expressing the recombination protein, wherein the expressed recombinant protein comprises one or more terminal mannose residues. Mgat1 deficient cell lines are described above in section (I).

The recombinant glycoprotein produced in the Mgat1 deficient cell line can be any suitable glycoprotein, including therapeutic proteins and protein biologics. For example, the recombinant protein can be, without limit, an antibody, a fragment of an antibody, a monoclonal antibody, a humanized antibody, a humanized monoclonal antibody, a chimeric antibody, an IgG molecule, an IgG heavy chain, an IgG light chain, an IgA molecule, an IgD molecule, an IgE molecule, an IgM molecule, a vaccine, a growth factor, a cytokine, an interferon, an interleukin, a hormone, a clotting (or coagulation) factor, a blood component, an enzyme, a nutraceutical protein, a functional fragment or functional variant of any of the forgoing, or a fusion protein comprising any of the foregoing proteins and/or functional fragments or variants thereof. In exemplary embodiments, the recombinant glycoprotein is a human protein.

Methods for producing recombinant protein are well known in the art, and additional teaching is provided by Ausubel et al., 2003 supra. In general, the recombinant protein is expressed from an exogenously introduced nucleic acid. As detailed above in section (I)(e), the nucleic acid encoding the recombinant protein may be extrachromosomal or the nucleic acid encoding the recombinant protein may be integrated into the genome.

Methods for culturing the cell line such that the recombinant protein is expressed are well known in the art. Appropriate media and culture systems are known in the art and commercially available. In one embodiment, the recombinant protein is produced by the cell lines disclosed herein via serum free suspension culture.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As used herein, the term "endogenous sequence" refers to a chromosomal sequence that is native to the cell.

The term "exogenous sequence" refers to a chromosomal sequence that is not native to the cell, or a chromosomal sequence whose native chromosomal location is in a different location in a chromosome.

The terms "editing," "genome editing," or "chromosomal editing" refer to a process by which a specific chromosomal sequence is changed. The edited chromosomal sequence may comprise an insertion of at least one nucleotide, a deletion of at least one nucleotide, and/or a substitution of at least one nucleotide.

A "gene," as used herein, refers to a DNA region (including exons and introns) encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

The term "heterologous" refers to an entity that is not native to the cell or species of interest.

The terms "nucleic acid" and "polynucleotide" refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The term "nucleotide" refers to deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

The terms "polypeptide" and "protein" are used interchangeably to refer to a polymer of amino acid residues.

The term "recombination" refers to a process of exchange of genetic information between two polynucleotides. For the purposes of this disclosure, "homologous recombination" refers to the specialized form of such exchange that takes place, for example, during repair of double-strand breaks in cells. This process requires sequence similarity between the two polynucleotides, uses a "donor" or "exchange" molecule to template repair of a "target" molecule (i.e., the one that experienced the double-strand break), and is variously known as "non-crossover gene conversion" or "short tract gene conversion," because it leads to the transfer of genetic information from the donor to the target. Without being bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized homologous recombination often results in an alteration of the sequence of the target molecule such that part or all of the sequence of the donor polynucleotide is incorporated into the target polynucleotide.

As used herein, the terms "target site" or "target sequence" refer to a nucleic acid sequence that defines a portion of a chromosomal sequence to be edited and to which a targeting endonuclease is engineered to recognize, bind, and cleave.

The terms "upstream" and "downstream" refer to locations in a nucleic acid sequence relative to a fixed position. Upstream refers to the region that is 5' (i.e., near the 5' end of the strand) to the position and downstream refers to the region that is 3' (i.e., near the 3' end of the strand) to the position.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the GenBank website. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

As various changes could be made in the above-described cells and methods without departing from the scope of the invention, it is intended that all matter contained in the above description and in the examples given below, shall be interpreted as illustrative and not in a limiting sense.

EXAMPLES

The following examples illustrate certain aspects of the invention.

Example 1: Disruption of Mgat1 in CHO Cells Using ZFNs

A. Preparation of ZFN Expression Vectors and ZFN mRNA Targeted to Mgat1

Figure 2A:
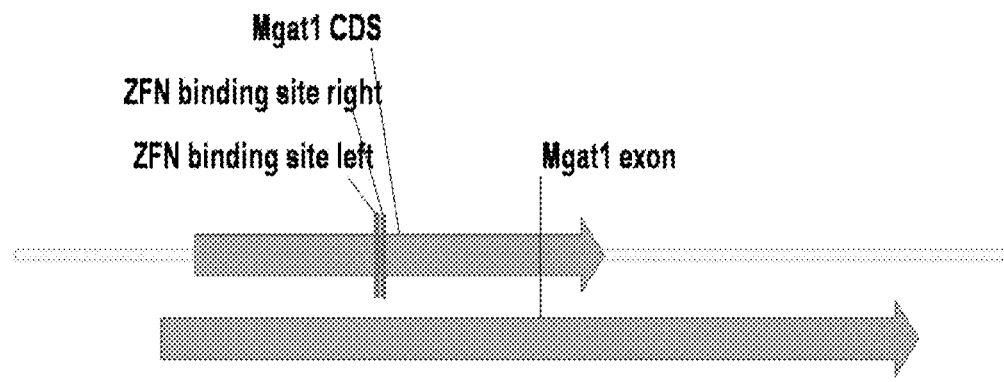
FIG. 2A illustrates the design of zinc finger nucleases (ZFNs) targeting Mgat1. Presented is a schematic illustration of the position that the ZFNs are designed to bind and cut in the Mgat1 coding region.

ZFN-mediated knockout techniques were employed to knock-out or inactivate the Mgat1 gene in CHO cells, thereby generating cells that produce proteins with a homogenous simple N-glycan profile containing terminal Man5 moieties. Mgat1 genomic contigs containing the Mgat1 locus (Xu et al., 2011, Nat Biotechnol, 29:735-741) were annotated using mouse homology. ZFNs targeting a specific site within the CHO Mgat1 coding region were designed using a proprietary algorithm. FIG. 2A diagrams the location of the target site in Mgat1. The target sequence in Mgat1 was 5'-AACAAGTTCAAGTTCccagcaGCTGTGGTAGTG-GAGGAC-3' (SEQ ID NO:1; ZFN binding sites in upper case and the cleavage site in lower case). Mgat1 ZFN expression construct were prepared using standard procedures and Mgat1 ZFN mRNA was produced from ZFN plasmid DNA as described in COMPOZR® Knockout Zinc Finger Nuclease (ZFN) (Sigma-Aldrich) product information using in vitro transcription, mRNA poly-adenylation, and capping methods. Briefly, the plasmid ZFN DNA was linearized and purified using phenol/chloroform DNA extraction. MessageMax™ T7 ARCA-Capped Message Transcription Kit (Cell Script Inc.) was used to cap the linearized DNA. A Poly(A) Polymerase Tailing Kit (Epi-Centre) was used to add a poly(A) tail. The ZFN mRNA was purified using the MEGAclear™ kit (Ambion).

B. Transfection of ZFNs Targeting Mgat1 in an IgG Producing CHO Cell Line

CHOZN® (GS −/−) cells (Sigma Aldrich) expressing recombinant anti-rabies human IgG were maintained as suspension cultures in EX-CELL® CHO CD Fusion media (Sigma-Aldrich) supplemented with 25 µM methionine sulphoximine (MSX). Cells were seeded at $0.5 \times 10^6$ cells/mL in bioreactor tubes one day prior to transfection. $1 \times 10^6$ cells in 150 µL growth media and 5 µg Mgat1 ZFN DNA or mRNA were used for each transfection. Transfections were conducted by electroporation at 140 V and 950 µF in 0.2 cm cuvettes. Electroporated cells were placed in 2 mL growth media in a 6-well plate static culture. On days 3 and 10 post-transfection, cells were removed from culture and genomic DNA was isolated using GeneElute™ Mammalian Genomic DNA Miniprep Kit (Sigma-Aldrich). A Cel-I nuclease assay, as described in COMPOZR® Knockout ZFN product information was conducted to determine the efficiency of the ZFN-mediated gene cleavage.

Figure 2B:
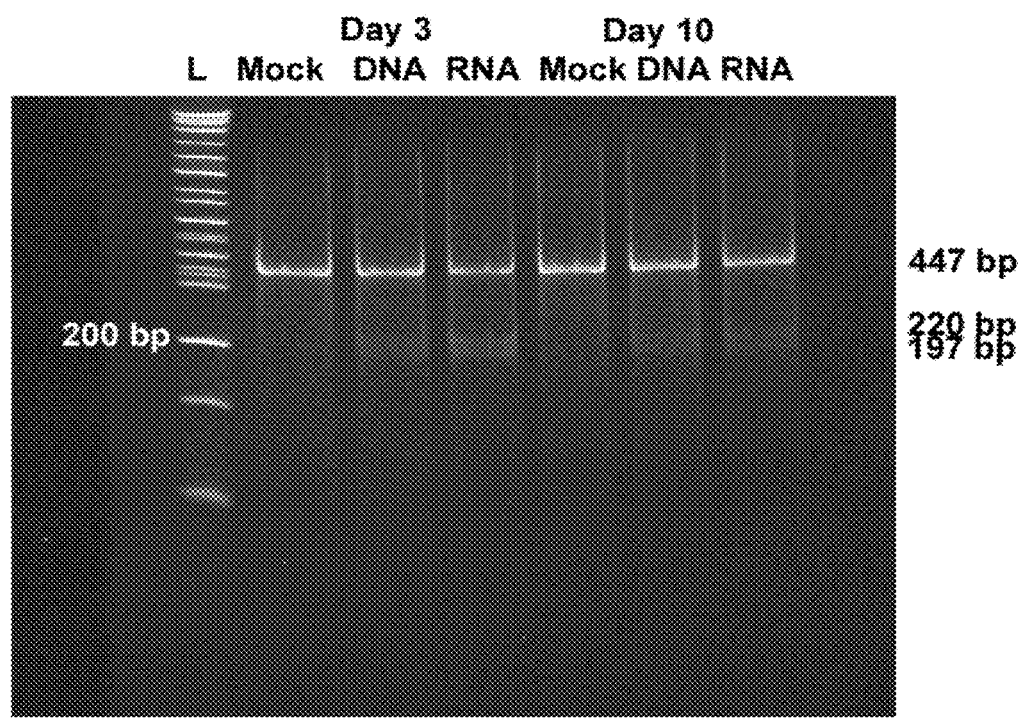
FIG. 2B shows validation of ZFNs targeting Mgat1 by a Cel1 nuclease assay. Shown are genomic DNA digests at Day 3 and Day 10 post-transfection from mock transfected cells, cells transfected with DNA, and cells transfected with RNA. Two DNA fragments, 220 and 197 bp, are present in both Day 3 and Day 10 post-transfection digests.

FIG. 2B depicts a gel showing the results of a Cel-I assay in ZFN-transfected (ZFN plasmid DNA or mRNA transfections) cell pools. Two cleavage fragments, 220 and 197 bp, were present in both Day 3 and Day 10 post-transfection in genomic DNA digests, indicating positive ZFN activity at both time points. ZFN activity on day 3 and day 10 was 8.8% and 9.6%, respectively. At both time points, cells transfected with RNA had slightly more intense bands. The stable ZFN activity over time implies no apparent cytotoxicity or growth inhibition related to Mgat1 disruption. In other words, no growth advantage of wildtype over ZFN modified cells was observed in the ZFN transfected population.

Example 2: Lectin Selection and Isolation of Single-Cell Clones

Mgat1 ZFN transfected cells were treated overnight with *Ricinus communis* agglutinin-I (RCA-I), a cytotoxic lectin that binds galactose but not mannose, in order to enrich for cells with disrupted Mgat1. On day 14 post-transfection, an aliquot of cells was plated for single cell cloning using FACS for viable cells. Cells were plated at one cell per well using a FACSAria™ III cell sorter (Becton-Dickinson) in 96-well tissue culture treated plates (Corning) in Ham's-F12 nutrient mix supplemented with 10% Fetal Bovine Serum (FBS) and 4 mM L-glutamine. The remaining cells were expanded until day 18 and then seeded at $1 \times 10^6$ cells/mL in T suspension culture flasks (Coring). Cells were incubated with 10 µg/mL final concentration of RCA-I in growth media overnight, then washed with PBS and returned to growth media. Cells were expanded to T flasks and cultured for 10 days and then plated for single-cell cloning as described above. Ten days post RCA-I treatment, cells were assayed for ZFN activity.

Figure 3:
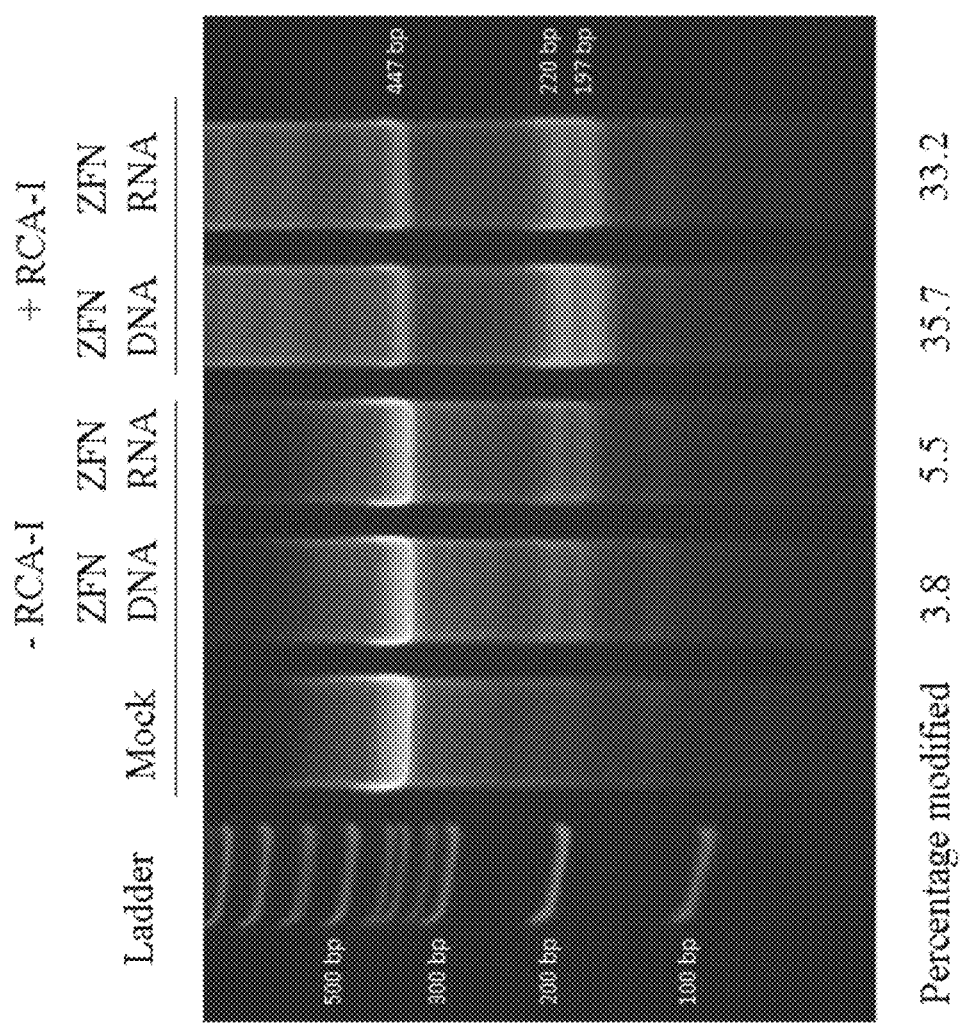
FIG. 3 presents Cel1 analysis before and after RCA-I enrichment. Shown are genomic DNA digests of cells transfected with DNA or RNA before and after RCA-I enrichment, as well as mock transfected cells. The percentage modified, as determined by densitometry, is listed under each lane.

FIG. 3 depicts a gel showing the results of a Cel-I assay in ZFN-transfected cell pools before and after RCA-1 enrichment. Cells selected with RCA-I displayed ZFN activity of about 33-36% compared to 3.8-5.5% for unselected cells, indicating successful enrichment for Mgat1 disrupted cells.

Example 3: Glycoprofiles of Secreted Recombinant Anti-Rabies Human IgG

A relatively high-throughput SEC-MS (Waters Acquity UPLC®/Q-Tof Premier™) workflow was used for glyco-analysis. The work flow utilized Protein-A purification of IgG from cell culture supernatants followed by accurate mass analysis of intact IgG heavy chain constituents. Protein A purification was performed using a 96-well filter plate with 50 µl Protein A resin and 750 µl clone supernatant per well. The IgG was eluted with 100 µl of 25 mM citrate, pH 3.0. Mass data analysis was performed by deconvolution and data processing performed in an automated fashion using BiopharmaLynx™ software (Waters). Glycopeptide forms were confirmed by trypsin digest of select samples and verification of glycan identification and relative distribution (reported as a % of total glycans) at the glycopeptide level by MALDI-TOF.

Figure 4A:
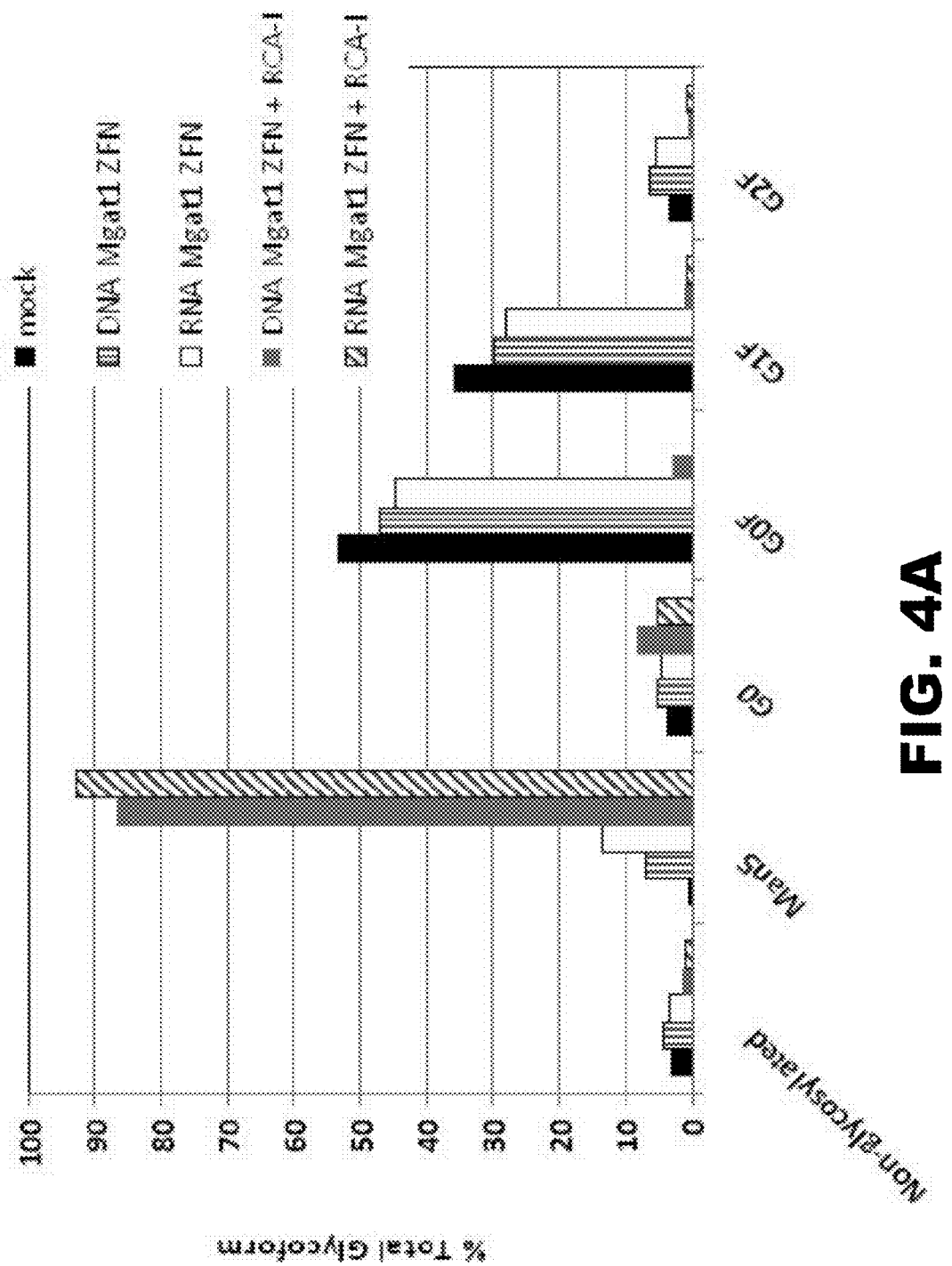
FIG. 4A shows the IgG glycoprofiles of Mgat1 ZFN transfected cells with or without RCA-I enrichment. Plotted is the percent of each glycoform (Man5, G0, G0F, G1F, and G2F) in IgGs produced by mock transfected cells, cells transfected with ZFN DNA or RNA without RCA-I selection, and cells transfected with ZFN DNA or RNA with RCA-I selection.
Figure 4B:
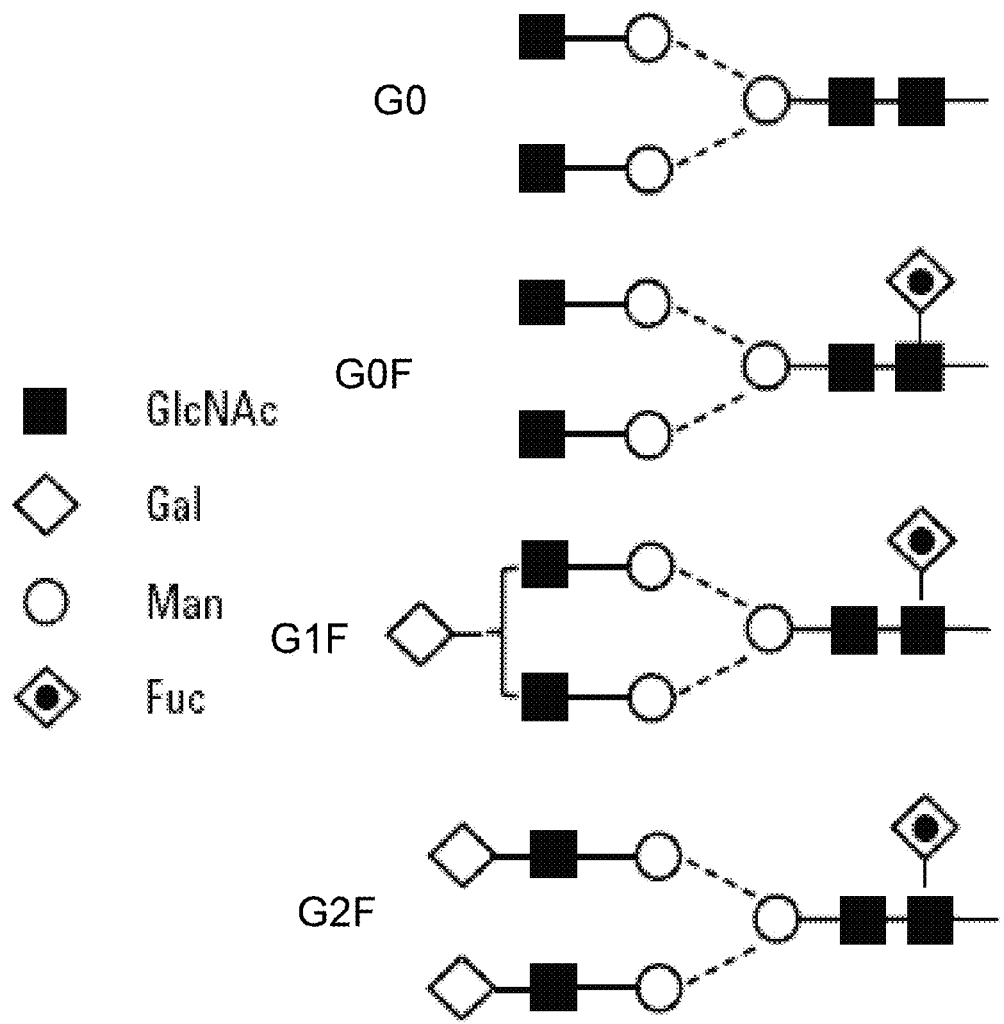
FIG. 4B diagrams the structure of G0, G0F, G1F, and G2F glycoforms.

The glycoprofiles of the secreted recombinant anti-rabies human IgG were assessed for each pool of cells (ZFN transfected and mock transfected, with or without RCA-I selection). The RCA-I enriched pools displayed increased levels of the Man5 glycoform relative to cells not exposed to RCA-I (FIG. 4A). The mock transfected cells demonstrated 0.3% Man5 compared with 13.7% for the Mgat1 ZFN transfected cells and 92.8% for the ZFN transfected cells enriched via RCA-I selection. The G0F and G1F glycoforms were most abundant in the mock transfected cells and the ZFN transfected cells that were not subjected to RCA-I enrichment.

Example 4: Genotype Characterization of Mgat1 Modified Single-Cell Clones

Genomic DNA was isolated from cultures of the single-cell clones (either IgG producing or the host GS (−/−) cell lines). A portion of the Mgat1 gene was amplified by PCR and the PCR products were cloned using the TOPO system (Life Technologies, Carlsbad, Calif.). Samples were prepared for DNA sequencing. A minimum of 10 TOPO clones were sequenced for genotypic characterization.

Figure 5:
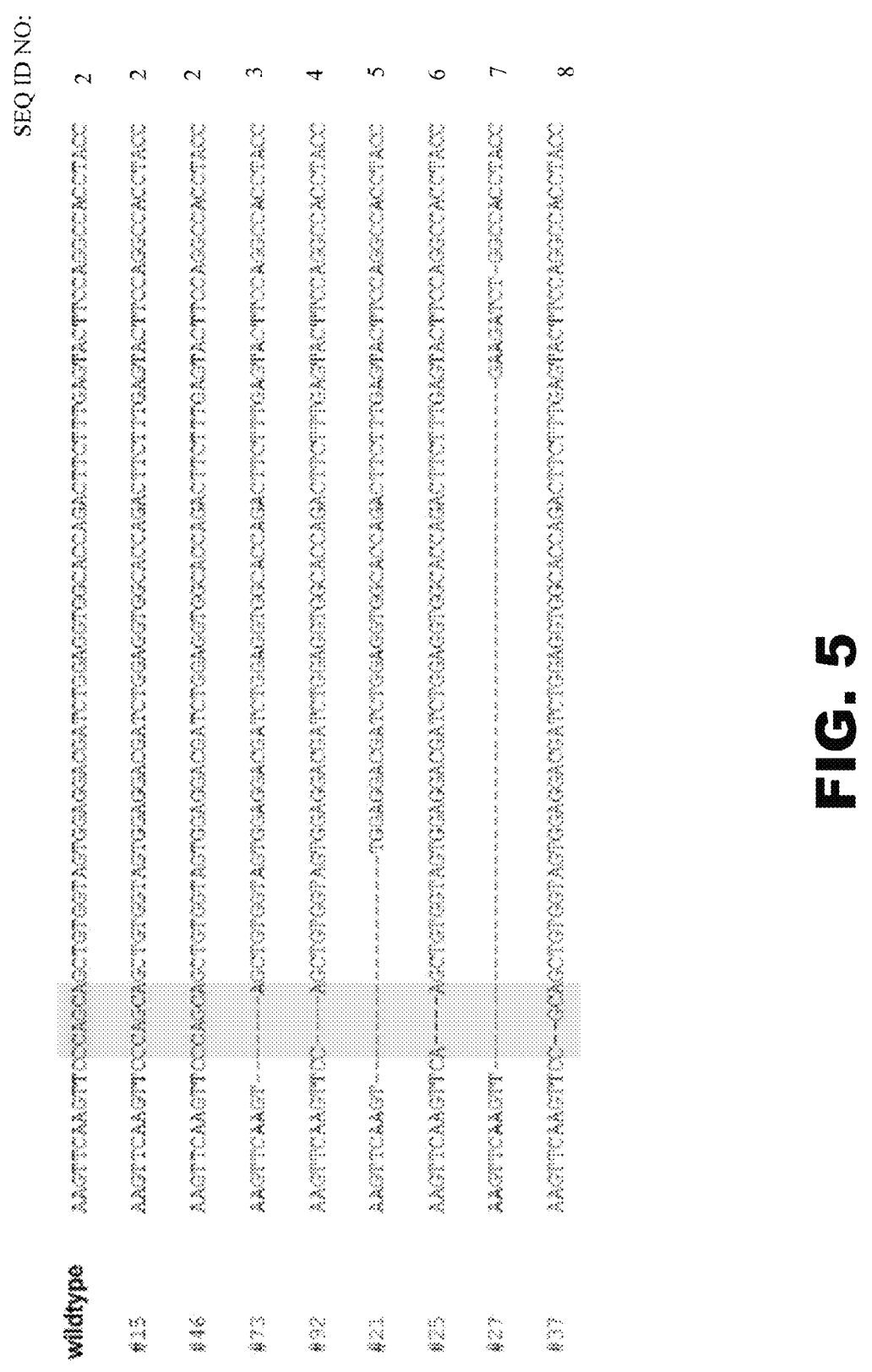

In order to compare the frequencies of Mgat1 modified clones in presence or absence of RCA-I enrichment, ZFN-transfected cells cultured with or without RCA-I were single-cell cloned by FACS, as described above. For the non-enriched pools, two clones out of 76 (2.63%) had short deletions in the Mgat1 gene (see FIG. 5 and Table 1; clones #73 and #92). Initial sequencing of nested PCR products from cell lysate obtained using QuickExtract™ DNA Extraction Solution (Epicentre) indicated that all clones (52/52) from the RCA-I enriched population contained disrupted Mgat1 gene sequences. The sequencing of these clones revealed deletion in Mgat1 from 2 bp deletions to 55 bp deletions (see FIG. 5 and Table 1, clones #21, #25, #27, and #37). Each clone contained one disrupted allele, with no wildtype sequence detected. Thus, the genotype of these cells is MGAT-1 (−/0) and GS (−/−).

TABLE 1

Genotype of Single-Cell Clones of Mgat1 Knock-Out IgG-Producing CHO Cell Line

| Clone ID | Allele 1 | Allele 2 | Genotype |
| --- | --- | --- | --- |
| #73 | 7 bp deletion | Not detected | Knockout |
| #92 | 4 bp deletion | Not detected | Knockout |
| #21 | 18 bp deletion | Not detected | Knockout |
| #25 | 4 bp deletion | Not detected | Knockout |
| #27 | 55 bp deletion | Not detected | Knockout |
| #37 | 2 bp deletion | Not detected | Knockout |

Figure 6:
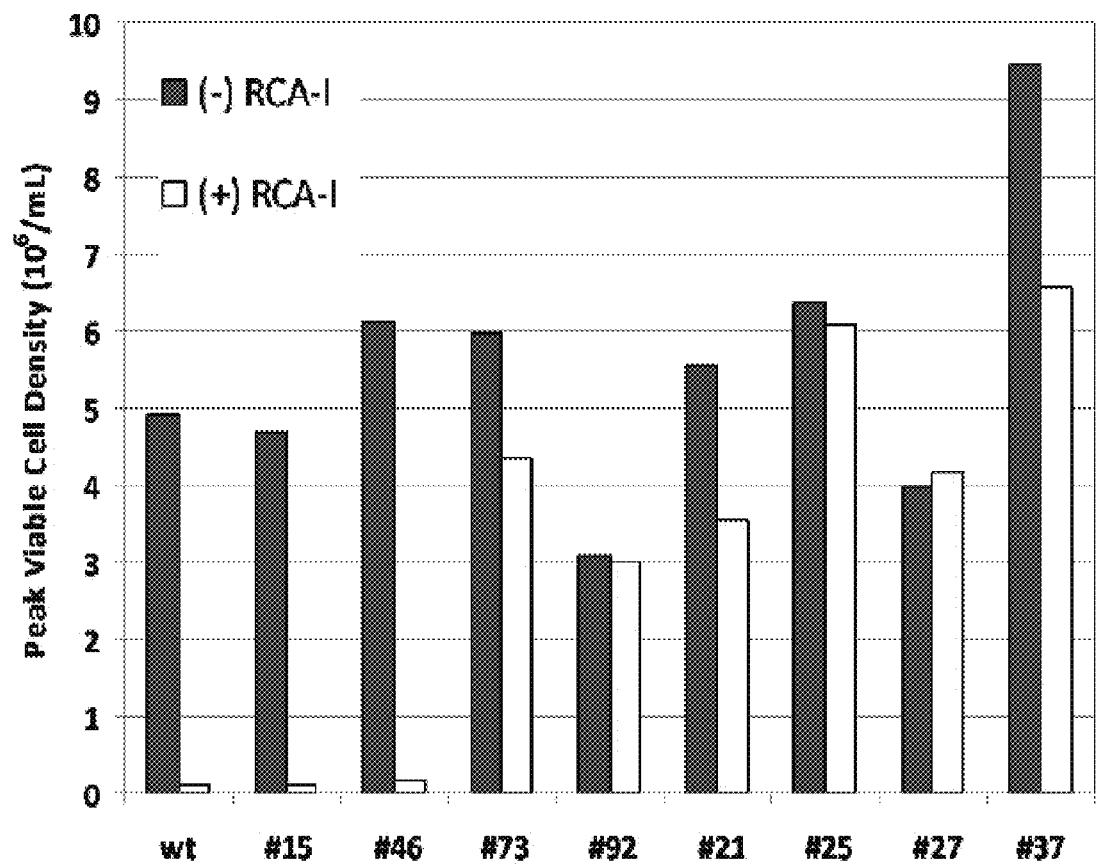
FIG. 6 illustrates the insensitivity of the Mgat1 knock-out clones to RCA-I. Plotted is the peak viable cell density in batch cultures of wildtype (wt, #15, #46) and Mgat1 knock-out (#73, #92, #21, #25, #27, #37) clones when grown in the absence or presence of RCA-I.

The following IgG producing Mgat1 knockout clones were selected for further characterization: two clones isolated without RCA-I selection (clones #73 and #92); two clones that went through the ZFN transfection process that retained the wild type sequence (#15 and #46); and four of the RCA-I selected clones (#21, #25, #27, and #37), with a range of deletion lengths. None of these knockout clones exhibited sensitivity to RCA-I (FIG. 6), nor were significant changes in the distribution of IgG productivity or growth observed.

Example 5: Characterization of Mgat1 Knock-Out IgG Producing Cell Clones

Figure 7A:
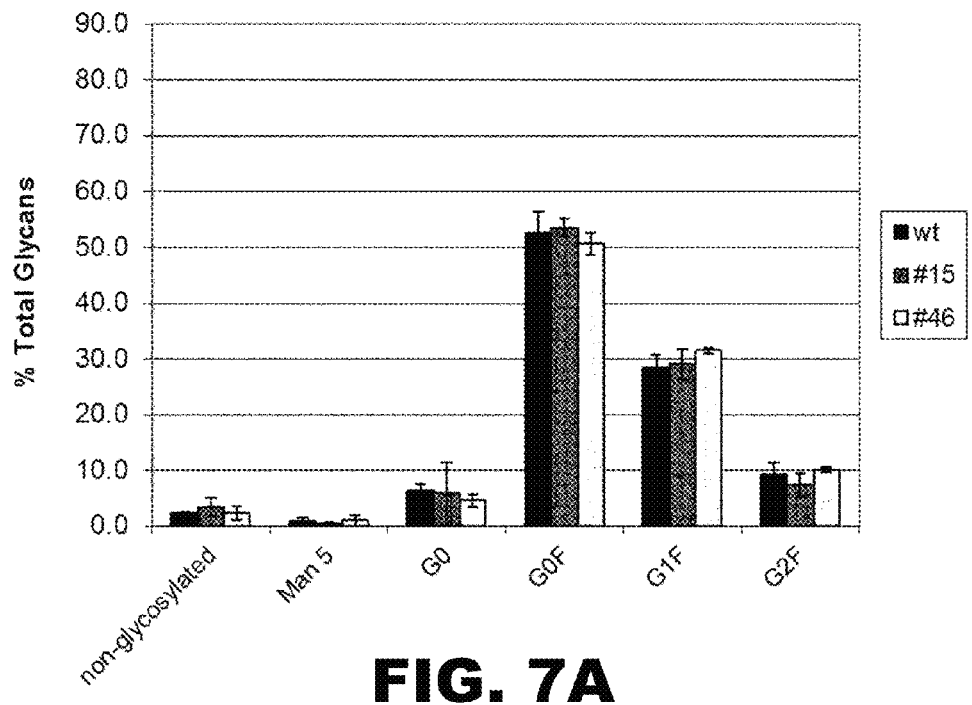
FIG. 7A shows the IgG glycoprofiles of wildtype and Mgat1 knock-out IgG producing clones. Plotted is the percentage of the different glycoforms in IgG samples harvested on Day 5 from the non-transfected (wt) and two wildtype (#15, #46) clones.
Figure 7B:
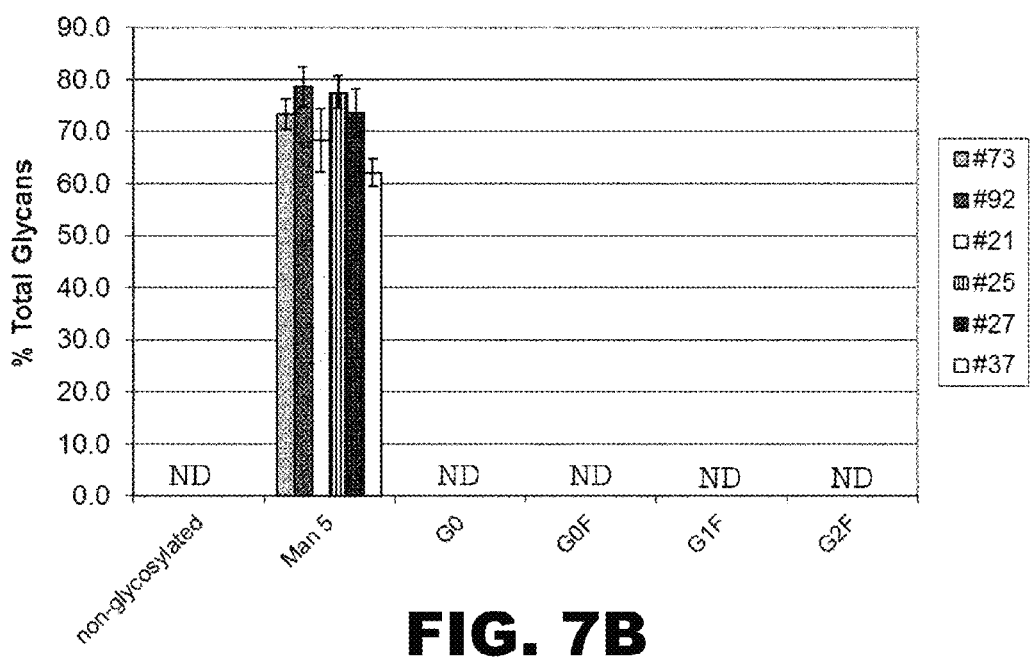
FIG. 7B shows the IgG glycoprofiles of Mgat1 knock-out IgG producing clones. Plotted is the percentage of the different glycoforms in IgG samples harvested on Day 5 from the six Mgat1 knock-out (#73, #92, #21, #25, #27, #37) clones. ND=not detected.
Figure 7C:
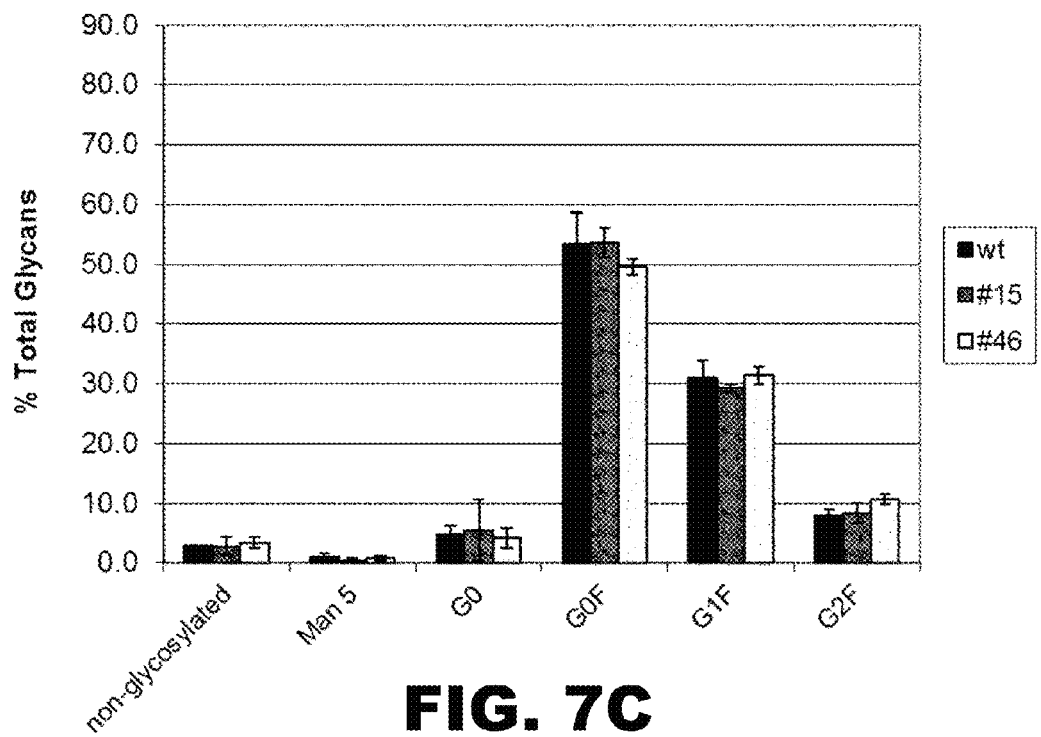
FIG. 7C shows the IgG glycoprofiles of wildtype and Mgat1 knock-out IgG producing clones. Plotted is the percentages of the different glycoforms in IgG samples harvested on Day 8 from the non-transfected (wt) and two wildtype (#15, #46) clones.
Figure 7D:
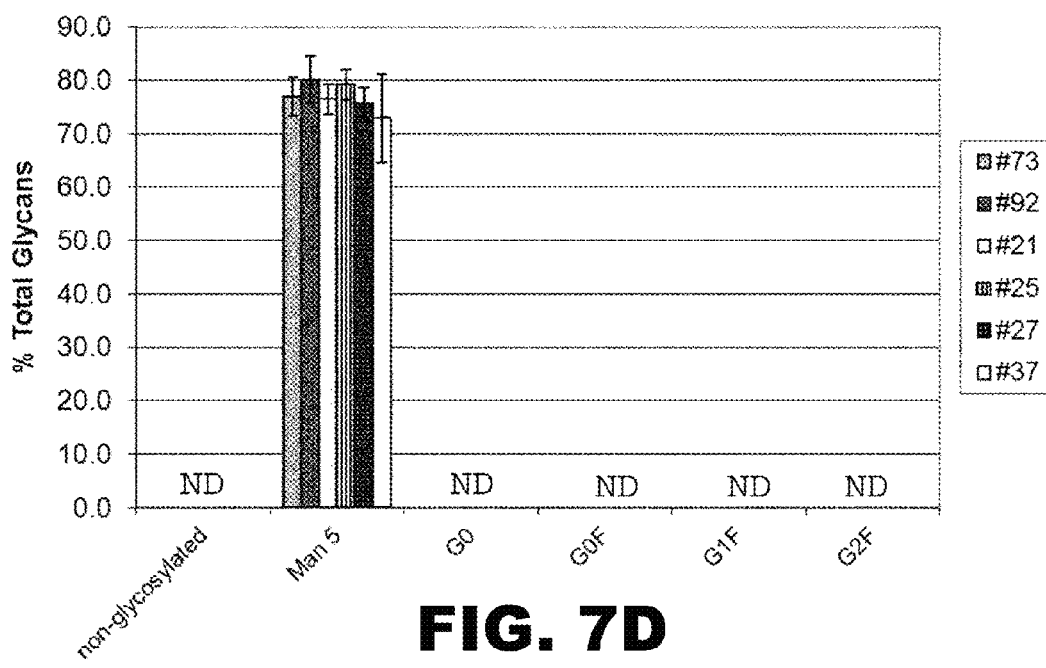
FIG. 7D shows the IgG glycoprofiles of Mgat1 knock-out IgG producing clones. Plotted is the percentage of the different glycoforms in IgG samples harvested on Day 8 from the six Mgat1 knock-out (#73, #92, #21, #25, #27, #37) clones. ND=not detected.

The glycoprofiles of the secreted recombinant anti-rabies human IgG were assessed (essentially as detailed above in Example 3) for each of the above-mentioned single cell clones. FIG. 7A,B presents the glycoprofiles of wildtype and knock-out clones, respectively, in Day 5 batch cultures, and FIG. 7C,D show the glycoprofiles of wildtype and knock-out clones, respectively, in Day 8 batch cultures. The most abundant glycan species is Man5 in the Mgat1 knock-out clones, whereas the wildtype clones displayed the highest G0F peaks. The % Man5 is significantly higher in the Mgat1 knock-out clones (p<0.0001, unpaired t-test with Welch's correction).

Figure 8A:
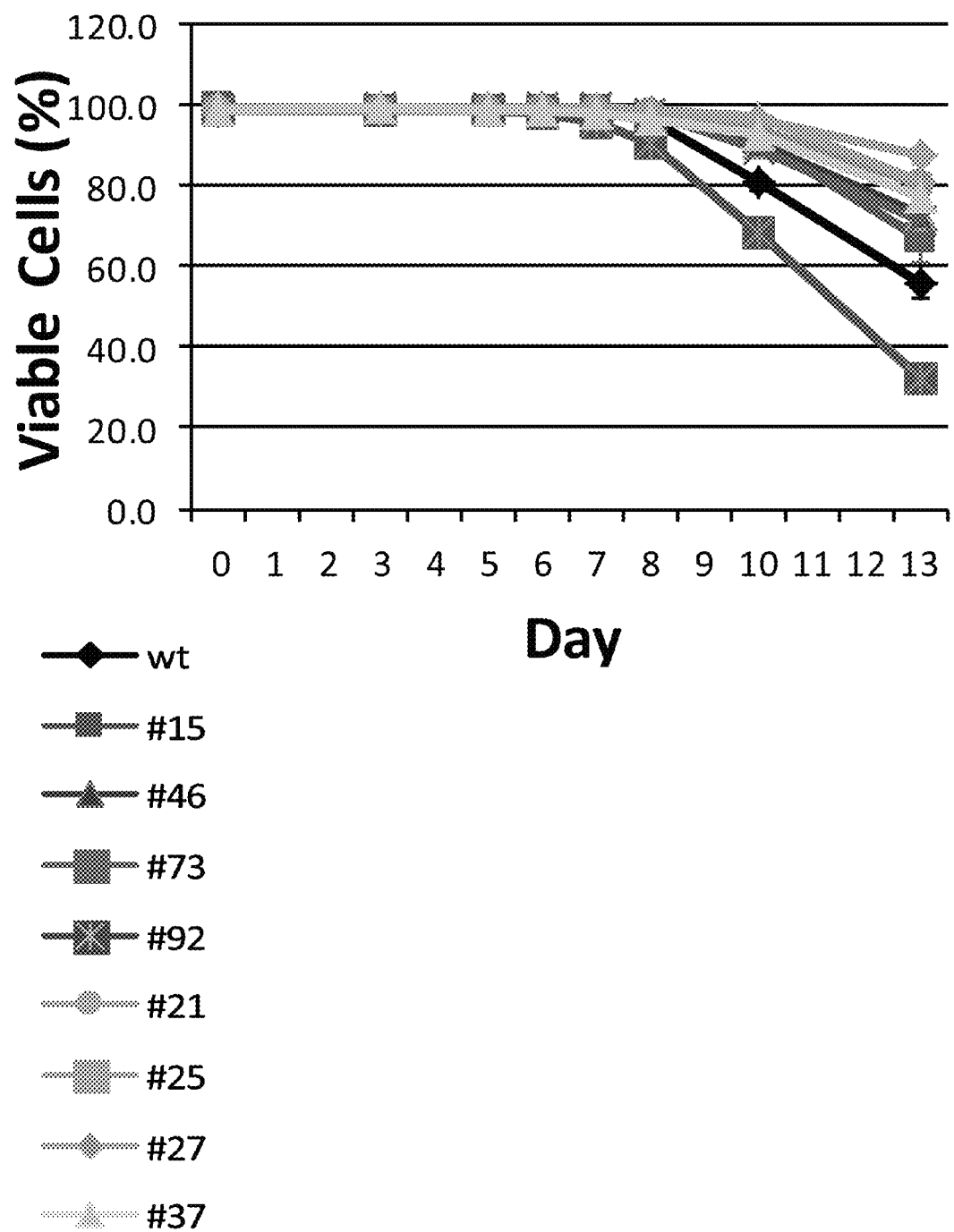
FIG. 8A presents the percent of viable cells in the wildtype (wt, #15, #46) and Mgat1 knock-out (#73, #92, #21, #25, #27, #37) clones over 13 days in batch culture.
Figure 8B:
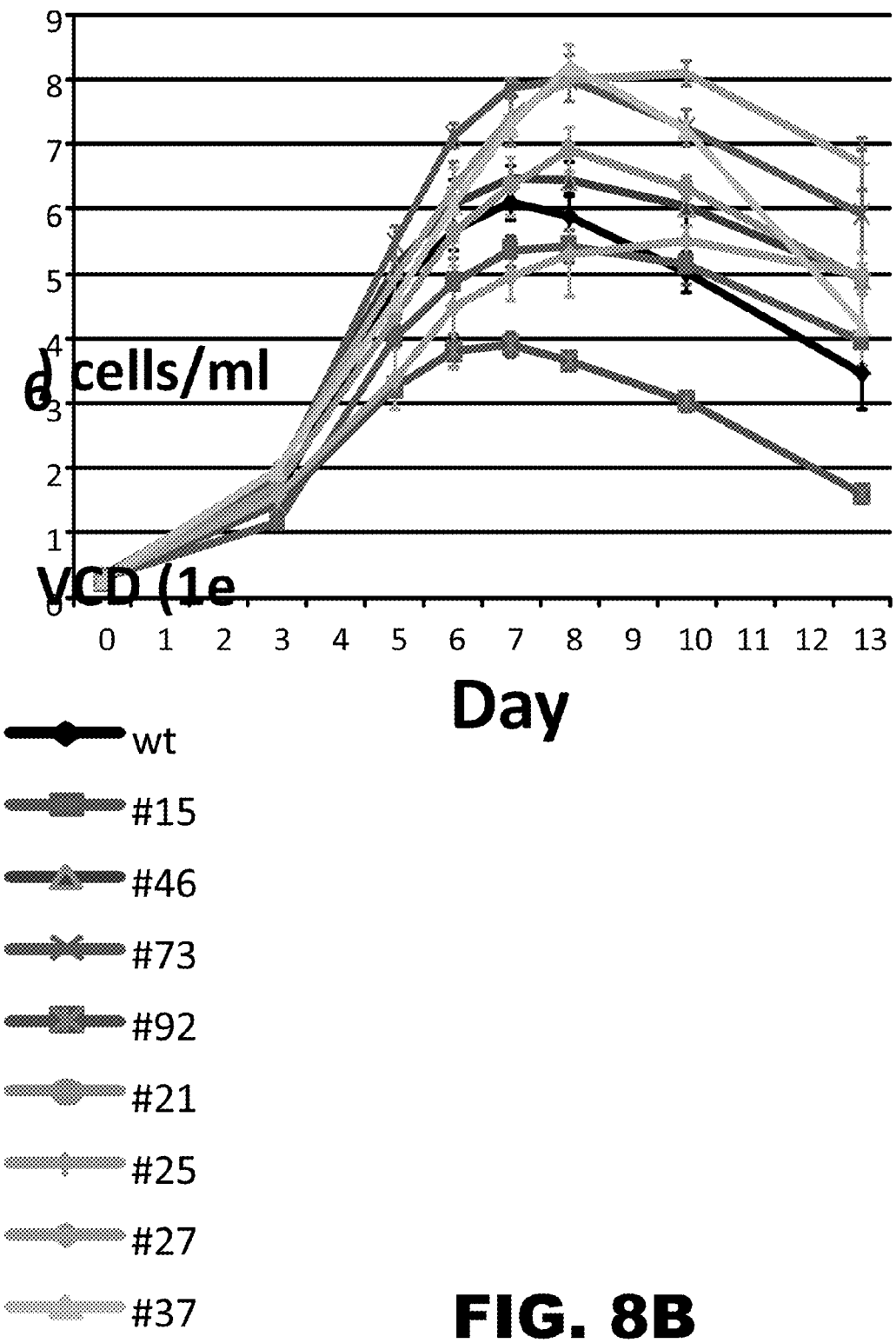
FIG. 8B shows the viable cell density in batch cultures of wildtype (wt, #15, #46) and six Mgat1 knock-out (#73, #92, #21, #25, #27, #37) clones over 13 days in batch culture.

To analyze the growth and productivity of the Mgat1 knock-out clones, cells were seeded at $0.3 \times 10^6$ cells/ml in 30 mL of growth media in TPP bioreactor tubes in duplicates. Cell density and viability were determined using a ViCell Cell Viability Analyzer (Beckmann Coulter). As shown in FIG. 8A,B, the Mgat1 knock-out cell clones exhibited the same or improved growth as measured by cell viability and cell density over time compared with cells having wildtype Mgat1.

Figure 9:
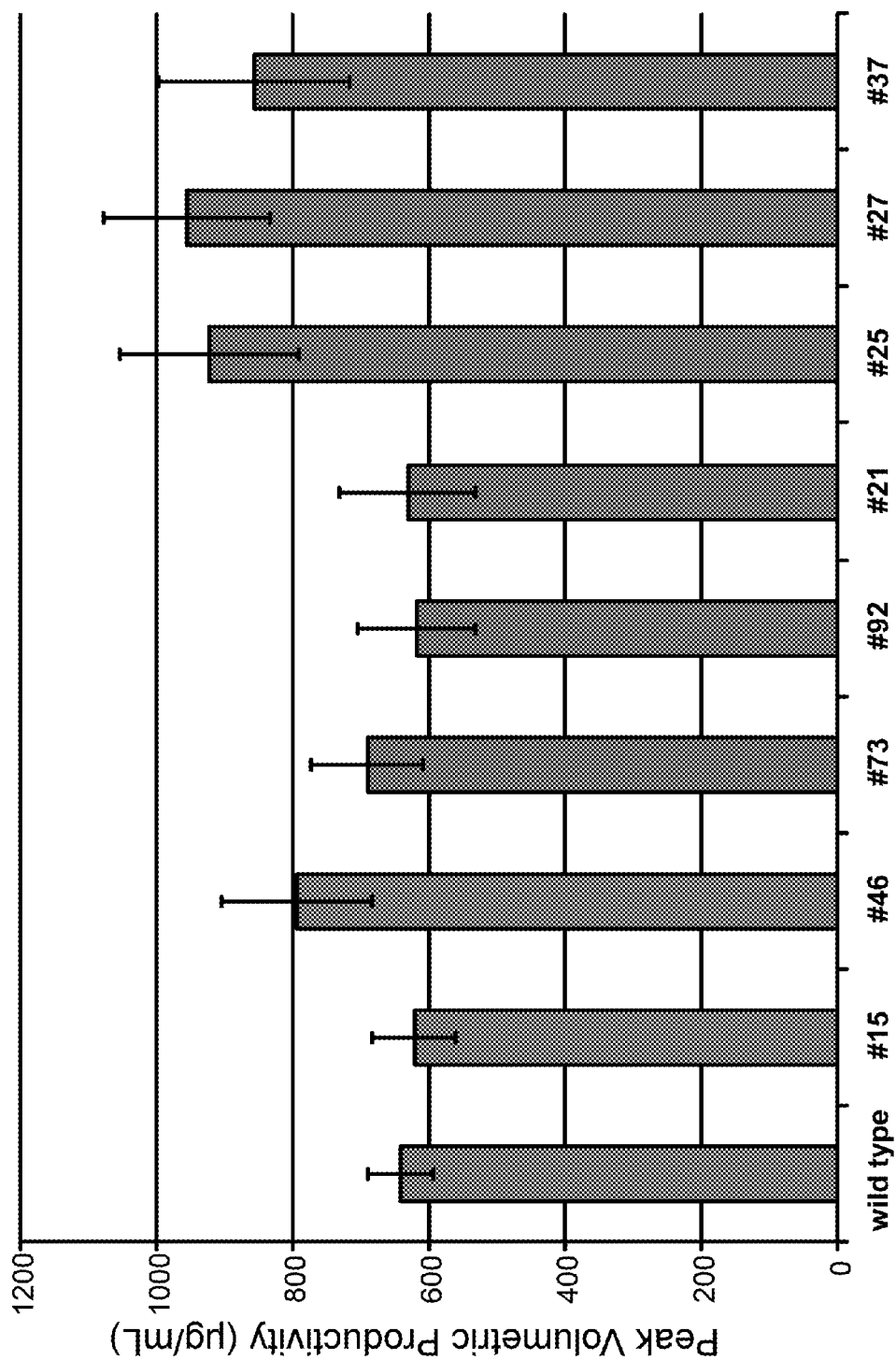
FIG. 9 shows the IgG productivity of wildtype and Mgat1 knock-out clones. Plotted is the peak volumetric productivity in the wildtype (wt, #15, #46) and the Mgat1 knock-out (#73, #92, #21, #25, #27, #37) clones.

Volumetric IgG productivity was determined by interferometry using a ForteBio OCTET® analyzer (Pall Life Sciences). As shown in FIG. 9, the Mgat1 knock-out cell clones exhibited the same or improved peak volumetric productivity as wildtype cells.

Example 6: Isolation of Mgat1 Knock-Out Clones in a CHO Host Cell Line

To further evaluate this method for biopharmaceutical applications, the ZFN transfection and clone isolation was repeated using a CHO K1 GS (−/−) host cell line. A host cell line with GS (−/−) (CHOZN® Sigma-Aldrich) was transfected with Mgat1 ZFN mRNA essentially as described above in Example 1. Upon confirmation of ZFN activity using the Cel-1 assay, the transfected cells were single-cell cloned using limiting dilution at 0.5 cell/well essentially as described above in Example 2. Clonality and growth were microscopically verified on Day 7 and Day 14 post plating, respectively. These cells were not treated with RCA-I for additional selection.

Five out of 90 (5.6%) clones generated from the CHOZN® GS (−/−) host cell line contained Mgat1 disruptions. The deletions identified in these clones, generated without RCA-I enrichment, were from 7 to 28 bp (see Table 2). As observed with the IgG-producing clones, these parental clones have only one disrupted allele and no wildtype sequence was identified. A lectin cytotoxicity assay was conducted using RCA-I, and similar to the IgG producing clones, no cytotoxicity was observed for any of the Mgat1 knock-out clones.

TABLE 2

Genotype of Single-Cell Clones of Mgat1 Knock-Out CHO Host Cell Line

| Clone ID | Allele 1 | Allele 2 | Genotype |
| --- | --- | --- | --- |
| AB4 | 24 bp deletion | Not detected | Knockout |
| BC9 | 7 bp deletion* | Not detected | Knockout |
| BD7 | 10 bp deletion | Not detected | Knockout |
| BH11 | 157 bp deletion replaced by 104 bp insertion | Not detected | Knockout |
| CG10 | 28 bp deletion | Not detected | Knockout |

Example 7: Stable IgG Expression and IgG Glycoprofiling of the Mgat1 Knock-Out Host Cell Lines Five Mgat1 knockout host cell line clones (listed in Table 2) were transfected with an expression vector containing human anti-rabies IgG coding sequences and a recombinant hamster GS expression cassette. Forty-eight hours prior to transfection, cells were seeded at $5\times10^5$ cells/mL. Transfections were conducted by electroporation as described in Example 1 using 30 μg plasmid DNA. Electroporated cells were placed into suspension 25 cm$^2$ cell culture flasks in 5 mL growth medium. Cells were transferred in media deficient of L-glutamine 48 hours post transfection and cultured at 37° C. in 5% $CO_2$ until selection was complete (12-14 days) and stably transfected cultures were established. In a separate transfection, cells were plated at 5000 cells/well in 96-well plates in 200 μL for minus glutamine selection and scaled up upon completion of selection to "mini pool" cultures to 24-well (1 mL), 25 cm$^2$ flasks (5 mL) and TPP tubes (30 mL). From these stable lines, TPP cultures were set up similarly as previously described, and cultures fed 2 g/L glucose along with a chemically-defined feed on day 4 and day 7. Cultures were harvested on day 8, and supernatant clarified by centrifugation at 3400 rpm and subsequently dialyzed against 1×PBS using a Spectra/Pore 4 membrane dialysis tubing (MWCO 12 kDa, Spectrum Labs, Rancho Dominguez, Calif.) for 24 hours at 4° C., and purified on a ÄKTA FPLC system (GE healthcare, Pittsburgh, Pa.) using a 1-ml HiTrap Protein A Fast Flow column (GE Healthcare). IgG was eluted in 0.1M citrate pH 3.0 and fractions immediately neutralized by addition of ¹⁄₁₀ volume 1.0M Tris HCl pH9.0. Glycoprofiling was performed essentially as described in Example 3.

Anti-rabies IgG produced in all five Mgat1 knock-out host cell lines demonstrated highly similar glycoprofiles, with Man5 being the predominant species with no complex glycans detected. MS analysis demonstrated a mass shift of the predominant glycan peak in the Mgat1 knock-out cell lines (i.e., 50168-50172) compared to the wildtype cells (i.e., 50400). The IgG produced in BC9 and BH11 "mini-pools" demonstrated comparable glycoprofiles to their "bulk" selected stable pools.

What is claimed is:

1. A genetically modified cell line deficient in mannosyl (alpha-1,3-)-glycoprotein beta-1,2-N-acetylglucosaminyl-transferase I (Mgat1) comprising a deletion of less than 200 bp in the coding region of a chromosomal sequence encoding Mgat1.

2. The genetically modified cell line of claim 1, wherein the cell line comprises an insertion in addition to the deletion in the coding region of the chromosomal sequence encoding Mgat1.

3. The genetically modified cell line of claim 1, wherein the cell line produces a reduced level of Mgat1 protein.

4. The genetically modified cell line of claim 1, wherein the cell line produces no Mgat1 protein.

5. The genetically modified cell line of claim 1, wherein the chromosomal sequence encoding Mgat1 is modified using a targeting endonuclease-mediated genome editing technology.

6. The genetically modified cell line of claim 5, wherein the targeting endonuclease is a zinc finger nuclease, a transcription activator-like effector nuclease (TALEN), a meganuclease, or a site-specific endonuclease.

7. The genetically modified cell line of claim 5, wherein the targeting endonuclease is a zinc finger nuclease.

8. The genetically modified cell line of claim 1, wherein the cell line further comprises a deficiency in dihydrofolate reductase (DHFR), hypoxanthine-guanine phosphoribosyl-transferase (HPRT), or a combination thereof.

9. The genetically modified cell line of claim 1, wherein the cell line is a Chinese Hamster Ovary (CHO) cell line.

10. The genetically modified cell line of claim 9, wherein the CHO cell line has a genotype of Mgat1 (−/0).

11. The genetically modified cell line of claim 1, wherein the cell line expresses at least one glycoprotein comprising one or more terminal mannose residues.

12. The genetically modified cell line of claim 1, wherein the cell line has a growth rate comparable to that of a cell line having no deficiency in Mgat1.

13. The genetically modified cell line of claim 1, wherein the cell line produces a level of protein comparable to that of a cell line having no deficiency in Mgat1.

14. A method for producing a recombinant protein having one or more terminal mannose residues, the method comprising:
   a) introducing a nucleic acid encoding the recombinant protein into the cell line of claim 1; and
   b) expressing the recombinant protein.

15. The method of claim 14, wherein the cell line produces no Mgat1 protein.

16. The method of claim 14, wherein the cell line is a Chinese Hamster Ovary (CHO) cell line.

* * * * *

SEQUENCE LISTING

<160> NUMBER OF SEQ ID NOS: 8

<210> SEQ ID NO 1
<211> LENGTH: 39
<212> TYPE: DNA
<213> ORGANISM: Cricetulus griseus

<400> SEQUENCE: 1
aacaagttca gttcccagc agctgtggta gtggaggac                            39

<210> SEQ ID NO 2
<211> LENGTH: 85
<212> TYPE: DNA
<213> ORGANISM: Cricetulus griseus

<400> SEQUENCE: 2
aagttcaagt tcccagcagc tgtggtagtg gaggacgatc tggaggtggc accagacttc    60
tttgagtact tccaggccac ctacc                                         85

<210> SEQ ID NO 3
<211> LENGTH: 78
<212> TYPE: DNA
<213> ORGANISM: Cricetulus griseus

<400> SEQUENCE: 3
aagttcaagt agctgtggta gtggaggacg atctggaggt ggcaccagac ttctttgagt    60

```
acttccaggc cacctacc                                                   78

<210> SEQ ID NO 4
<211> LENGTH: 81
<212> TYPE: DNA
<213> ORGANISM: Cricetulus griseus

<400> SEQUENCE: 4
aagttcaagt tccagctgtg gtagtggagg acgatctgga ggtggcacca gacttctttg    60
agtacttcca ggccacctac c                                              81

<210> SEQ ID NO 5
<211> LENGTH: 67
<212> TYPE: DNA
<213> ORGANISM: Cricetulus griseus

<400> SEQUENCE: 5
aagttcaagt tggaggacga tctggaggtg gcaccagact tctttgagta cttccaggcc    60
acctacc                                                              67

<210> SEQ ID NO 6
<211> LENGTH: 81
<212> TYPE: DNA
<213> ORGANISM: Cricetulus griseus

<400> SEQUENCE: 6
aagttcaagt tcaagctgtg gtagtggagg acgatctgga ggtggcacca gacttctttg    60
agtacttcca ggccacctac c                                              81

<210> SEQ ID NO 7
<211> LENGTH: 30
<212> TYPE: DNA
<213> ORGANISM: Cricetulus griseus

<400> SEQUENCE: 7
aagttcaagt tgaagatctg gccacctacc                                     30

<210> SEQ ID NO 8
<211> LENGTH: 83
<212> TYPE: DNA
<213> ORGANISM: Cricetulus griseus

<400> SEQUENCE: 8
aagttcaagt tccgcagctg tggtagtgga ggacgatctg gaggtggcac cagacttctt    60
tgagtacttc caggccacct acc                                            83
```